(12) United States Patent  (10) Patent No.: US 9,119,700 B2
Boukhny  (45) Date of Patent: Sep. 1, 2015

(54) GRAPHICAL USER INTERFACE SYSTEM AND METHOD FOR REPRESENTING AND CONTROLLING SURGICAL PARAMETERS

(75) Inventor: Mikhail Boukhny, Laguna Niguel, CA (US)

(73) Assignee: Novartis AG, Basel (CH)

( * ) Notice: Subject to any disclaimer, the term of this patent is extended or adjusted under 35 U.S.C. 154(b) by 2696 days.

(21) Appl. No.: 11/000,216

(22) Filed: Nov. 30, 2004

(65) Prior Publication Data

US 2006/0114175 A1  Jun. 1, 2006

(51) Int. Cl.
| | | |
|---|---|---|
| *A61B 18/10* | (2006.01) | |
| *A61F 9/007* | (2006.01) | |
| *G06F 3/0484* | (2013.01) | |
| *A61B 17/00* | (2006.01) | |

(52) U.S. Cl.
CPC ........ *A61F 9/00745* (2013.01); *G06F 3/04847* (2013.01); *A61B 2017/00199* (2013.01); *A61B 2017/00225* (2013.01)

(58) Field of Classification Search
CPC ................... G06F 3/0488; G06F 2203/04808; G06F 3/048; G06F 3/04845
USPC ............................................ 606/1, 4, 34, 41
See application file for complete search history.

(56) References Cited

U.S. PATENT DOCUMENTS

| | | | |
|---|---|---|---|
| 5,455,766 A | | 10/1995 | Scheller et al. |
| 5,554,894 A | * | 9/1996 | Sepielli ......................... 307/119 |
| 5,997,528 A | | 12/1999 | Bisch et al. |
| 6,251,113 B1 | | 6/2001 | Appelbaum et al. |
| 6,442,440 B1 | * | 8/2002 | Miller ............................. 700/83 |
| 6,512,530 B1 | * | 1/2003 | Rzepkowski et al. ......... 715/833 |
| 6,583,796 B2 | * | 6/2003 | Jamar et al. .................... 715/804 |
| 6,671,535 B1 | * | 12/2003 | McNichols et al. ........... 600/407 |
| 6,783,523 B2 | * | 8/2004 | Qin et al. ........................... 606/1 |
| 2002/0045887 A1 | | 4/2002 | DeHoogh et al. |
| 2004/0024384 A1 | | 2/2004 | Novak |
| 2004/0158132 A1 | | 8/2004 | Zaleski |
| 2006/0149301 A1 | | 7/2006 | Claus |

FOREIGN PATENT DOCUMENTS

WO      WO 98/25556      6/1998

OTHER PUBLICATIONS

International Search Report for PCT/US2005/043,188, Publication No. W02006060423, 3 pages.

* cited by examiner

*Primary Examiner* — Aaron Roane

(74) *Attorney, Agent, or Firm* — Darien Reddick

(57) ABSTRACT

Graphical user interface system and method for displaying and controlling a surgical device, such as a device used in phacoemulsfication procedures. A graphical user interface is displayed on a display screen and includes one or more representations of operating parameters, such as aspiration rate, vacuum, and power that are used to control the surgical device. A parameter is adjusted by moving a portion of a representation from a first location on the display screen to a second location on the display screen to change the operating parameter and control the surgical device.

47 Claims, 23 Drawing Sheets

GRAPHICAL USER INTERFACE SYSTEM AND METHOD FOR REPRESENTING AND CONTROLLING SURGICAL PARAMETERS

TECHNICAL FIELD OF THE INVENTION

The invention relates generally to interfaces for surgical systems, and, more particularly, to graphical user interfaces for ophthalmic surgical systems that include representations of operating parameters that can be moved on a display screen to adjust and control the surgical systems.

BACKGROUND OF THE INVENTION

Modern day surgical systems, and in particular, modern day ophthalmic surgical systems are designed to monitor and display multiple parameters of a surgical device or instrument that is connected to the surgical system and controlled by the surgeon. Such systems can be complex given the multiple parameters that must be displayed and controlled by a surgeon. A typical ophthalmic surgical system can provide several different functions, such as illumination, phacoemulsification, irrigation and aspiration, vitrectomy and microscissor cutting, among others, and provide capabilities for interior and/or posterior segment surgery.

Certain known phacoemulsification systems allow for application of fixed ultrasound power, i.e., energy that is either on or off at a constant level. Improvements were made to these constant energy systems by allowing phacoemulsification power to be linearly controlled. In this instance, power is proportional to the displacement of the surgeon's foot pedal. In other words, more ultrasound power is provided in accordance with the linear or proportional control as the surgeon depresses the foot pedal.

Other known phacoemulsification systems use other modes of ultrasound power, such as pulse mode, in which phacoemulsification power is provided in periodic pulses of a constant duty cycle, but with amplitude increasing or being fixed with foot pedal displacement. Other known systems use a burst mode, in which power is provided at a constant amplitude, but with intervals of power reducing with foot pedal displacement.

Examples of known user interfaces for displaying and controlling operating parameters of a surgical device are shown in FIGS. 22 and 23. Known interfaces typically include several types of human actionable controllers or fields that occupy pre-defined and fixed positions on a display screen. The interface is manipulated by a surgeon to provide control signals to the surgical instruments which, in turn, control the mode and amount of power provided to a handpiece for delivering ultrasound power. More particularly, known control consoles typically include interfaces that have push buttons, arrows, switches, bars and/or knobs for setting desired numeric values of operating characteristics for the surgical system. Whether the parameter is constant or varies linearly can be represented by a horizontal line and a line at an angle, respectively.

For example, as shown in FIG. 22, a surgeon manually selects the power mode to be continuous from the selection bar 10, and then manually selects the maximum amount of continuous power 12 that should be provided. In this instance, the maximum continuous power is 40% of the maximum power or power limit. This selection is performed by pressing the up/down arrows 11. In this example, continuous power 12 varies linearly. Pressing on the field switches between linear and continuous (fixed) control of the value. The surgeon also manually selects a constant vacuum of 80 mm Hg 14 and a constant aspiration rate of 23 cc/min 16 using up/down arrows 11. The instantaneous values of the ultrasound power, vacuum and aspiration rate are shown in fields 20, 22 and 24. The system is then controlled by a foot pedal controller to remotely control the surgical instruments based on the selected parameters.

As a further example, shown in FIG. 23, a surgeon manually selects using the power mode to be a linear pulse mode, rather than a linear continuous mode, and manually selects the power limit of 70%, eight pulses per second (pps) 30 and that the pulses should be on 20% of the time 32. The surgeon also manually selects the vacuum limit 14 to linearly increase up to 300 mm Hg and the aspiration 16 to be constant at 45 cc/min. These adjustments are made in a similar manner as previously discussed by touching the up/down arrows 11 to increase or decrease the parameter value.

While known interfaces have been used to perform successful procedures in the past, they can be improved. Particularly, the visual and functional aspects of interfaces can be enhanced so that the representation and control of additional parameters and power modes do not result in unnecessarily complicated interfaces, thus providing useful interfaces that are visually organized and comprehensible. Interfaces should also be capable of effectively representing various operating parameters of various ultrasound driving modes, including continuous, linear, pulse, burst, and combinations or modifications thereof. Improvements can be equally applicable to other non-ultrasound surgical modalities, for example irrigation, aspiration, coagulation using high-frequency currents to coagulate tissue to stop bleeding, vitrectomy, a mode using guillotine mechanical cutter that uses a high speed miniature jet of warmed irrigation solution, and others. Further, it should be easier for a surgeon to manipulate the interface and exert proper control over the surgical devices during a surgical procedure, thereby enhancing the effectiveness and safety of the procedure.

BRIEF SUMMARY OF THE INVENTION

According to one embodiment, an interface for displaying parameters related to the operation of a surgical device on a display screen and controlling the parameters includes a graphical user interface that includes representations of the parameters. A surgeon can adjust the parameters by moving at least a portion of a representation of a parameter from a first location on the display screen to a second location on the display screen in order to control the operation of the surgical device.

In an alternative embodiment, a system for displaying parameters related to the operation of a surgical device on a display screen and controlling the parameters includes a display screen and a graphical user interface that includes representations of parameters that are related to the operation of the surgical device. The graphical user interface also includes a representation of stages of the phacoemulsification procedure. The representations of operating parameters are shown in the display screen relative to the representations of the stages of the phacoemulsification procedure.

According to a further alternative embodiment, an interface for displaying on a display screen and controlling a parameter related to the operation of a surgical device includes a graphical user interface that includes a representation of the operating parameter. A surgeon can adjust the parameter by moving at least a portion of the parameter representation between different locations on the display screen in order to control the manner in which the surgical device operates.

A further alternative embodiment is directed to a method of displaying and controlling operating parameters of a surgical device. Initially, a representation of a parameter related to the operation of the surgical device is generated and displayed on the display screen. The representation includes first and second ends, which represent minimum and maximum parameter values, respectively. A surgeon contacts an end of the representation and moves the contacted end from a first location to a different location on the display screen in order to control a value of the parameter.

In various embodiments, one or more representations can be linear and include first and second ends that represent respective minimum and maximum values of the parameter and fields that indicate the value of the parameter. The one or more representations can be displayed or programmed with different functions, such as a linear, logarithmic, exponential or polynomial function. The minimum value can be selected to be zero or an intermediate value, and the maximum value can be adjusted as necessary, thus providing more flexibility and control over operating parameters, and providing the ability to select and adjust the system so that power in continuous, linear, pulsed and burst modes can be utilized.

Further, the graphical user interface can be represented on the display screen with a representation of stages of a surgical procedure, such as an ophthalmic surgical procedure, which are represented as vertical dividers. A stage of the procedure is defined between two dividers, and can identify the beginning or end of a particular stage of the procedure, such as irrigation, aspiration and ultrasound power. The parameter representation can be adjusted by moving an end of the parameter representation along a vertical divider. The graphical user interface can also include a representation of a control member, such as a foot pedal, that is used to operate the surgical device. The parameter representation can also be displayed relative to the control member representation, and the control member representation can be moved to indicate the stage of the procedure and corresponding operating parameters that are invoked by displacement of the control member.

BRIEF DESCRIPTION OF THE DRAWINGS

A more complete understanding of embodiments and the advantages thereof may be acquired by referring to the following description, taken in conjunction with the accompanying drawings in which like reference numbers indicate like features and wherein.

DETAILED DESCRIPTION OF THE INVENTION

Figure 1:
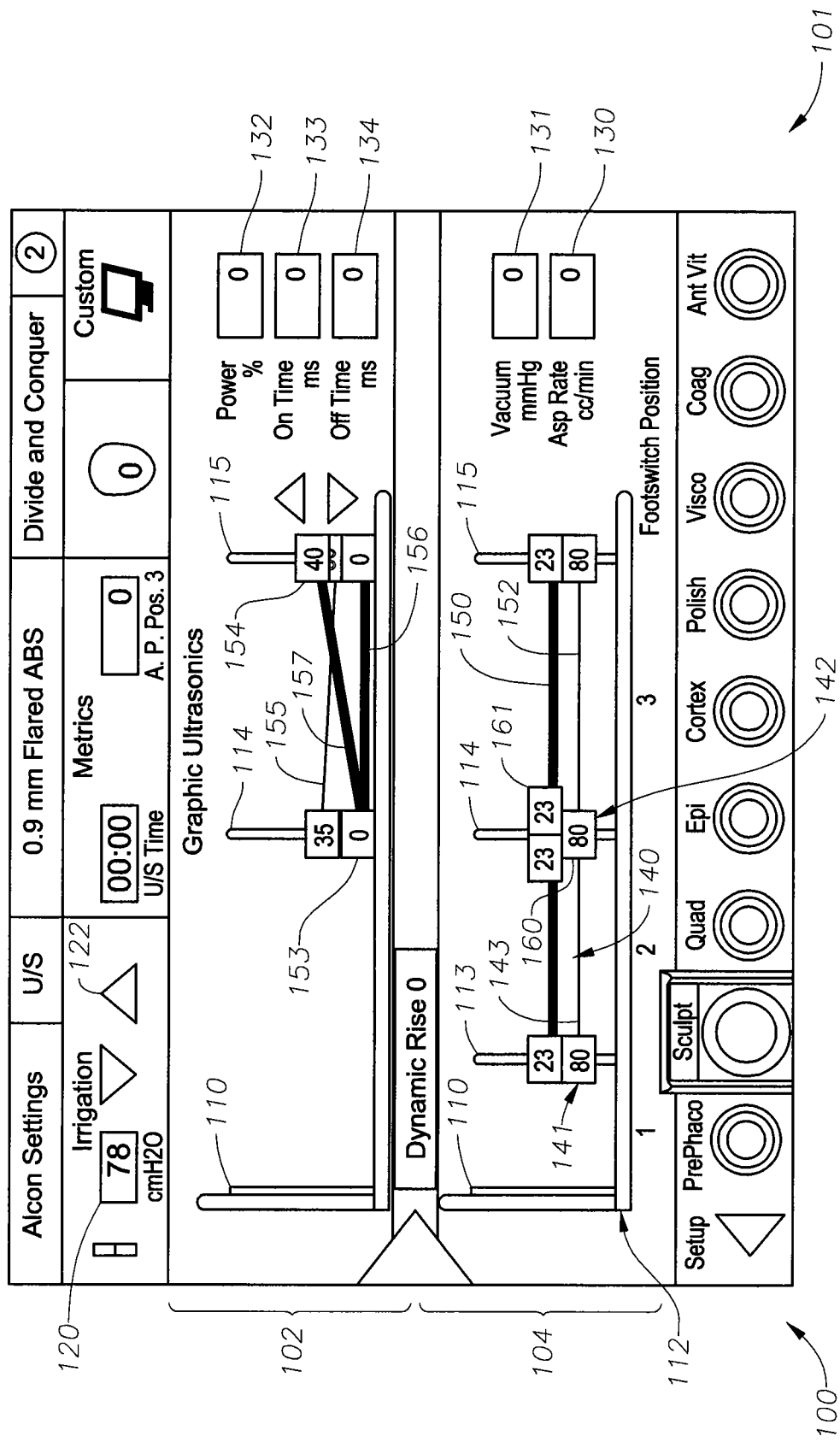
FIG. 1 illustrates a graphical user interface according to one embodiment that includes representations of parameters that are selected to provide continuous ultrasound power that varies linearly.

In the following description, reference is made to the accompanying drawings, that form a part hereof, and that show by way of illustration specific embodiments in which the present invention may be practiced. It is to be understood that changes may be made without departing from the scope of the embodiments.

Embodiments are directed to a graphical user interface that is presented on a display screen and that provides representations of parameters related to the operation to of a surgical device that is used in, for example, phacoemulsification procedures. Persons skilled in the art will appreciate that embodiments can be utilized with various other surgical procedures including, but not limited to, neurosurgery, where control of various instruments is also performed with a remote foot pedal. For purposes of explanation, not limitation, this specification describes embodiments related to phacoemulsification procedures and their associated operating parameters.

Embodiments provide a system and method for displaying and controlling operation parameters of a phacoemulsification surgical device. Exemplary parameters include aspiration flow rate, vacuum limit pressure and various power level parameters, such as minimum and maximum power (expressed as a % of maximum power), on time and off time. One or more representations of parameters are displayed on a display screen, such as a computer monitor or a screen of an integrated device or controller (generally, "display screen"), using a graphical user interface (generally "interface"). The surgeon controls the surgical device using a controller, such as a foot pedal or foot switch, which controls the operation of the surgical devices according to the corresponding operating parameters and parameter values represented on the display screen during different stages of a surgical procedure. The graphic representations can be easily and quickly programmed, monitored and manipulated by a surgeon. The representations can be adjusted to customize control over the operation of surgical devices and to provide specific operating parameter values or ranges of values during different stages of the procedure based on, for example, depression of the foot pedal. More particularly, the value and/or function of the parameters can change as the foot pedal is pressed to different levels, thus invoking a programmed set of operating parameters and values that appear on the display screen, relative to a particular controller position to control the surgical device. Embodiments provide these enhancements without the visual and functional complexities that would otherwise be associated with adding such capabilities to known interfaces.

FIGS. 1-11 illustrate graphical user interfaces and various settings of representations of operating parameters that can be programmed and used to control a surgical device. FIGS. 12-18 illustrate how control parameter settings that are represented on a display screen can be selected to control a surgical device based on a position of a controller, such as a foot pedal or switch (generally, "foot pedal"), which is depressed and released by a surgeon, thus controlling the stage of a procedure and invoking different control parameters and values.

FIG. 1 shows a screen shot of a graphical user interface 100 according to one embodiment that appears on a display screen 101. In one embodiment, the interface 100 is divided into two sections, a top section 102 and a bottom section 104. The top section 102 includes representations of power parameters, and the bottom section 104 includes representations of vacuum limit and aspiration rate, however, the information in the top and bottom sections 102 and 104 can be modified or switched as necessary. Further, the interface 100 may be vertically divided rather than being horizontally divided, or divided into more than two sections, or not divided at all.

The interface 100 includes representations of various operating parameters and a representation of a position of a controller, relative to stages of a surgical procedure that are invoked by pressing the foot pedal to different levels. The foot pedal representation 110 is shown as a vertical bar that is moveable along a horizontal scale 112 as the foot pedal is pressed and released by the surgeon.

For purposes of initially describing and illustrating the arrangements and adjustments to representations of surgical device parameters, FIGS. 1-11 show the foot pedal representation as being stationary, however, persons skilled in the art will appreciate that as the foot pedal is pressed to different positions, the foot pedal representation moves, and different operating parameters and values of operating parameters are invoked to control the surgical device. Pressing and releasing the foot pedal to different levels horizontally displaces the controller representation 110 along the scale 112 to apply various parameter values that are displayed on the interface relative to the foot pedal position. This specification refers to the foot pedal and foot pedal representation 110 occupying different positions or ranges of positions, which trigger surgical parameters depending, as controlled by the first pedal position actions. Various stages of surgical procedures correspond to various sets of the parameters. These sets of parameters can be accessed by pressing corresponding icons in the low row on the screen. FIG. 1-11 shows a set of parameters corresponding to the surgical step named "Pre-Phaco". Other surgical steps, for example Chop or Cortex, will generally have a different set of parameters associated with them. Some surgical steps may contain ultrasound parameters along with the fluidics parameters, flow and vacuum limit, while other steps will contain only fluidics parameters, yet other steps will not contain ultrasound or fluidics parameters. An example of the latter would be Coagulation surgical step (not show), which will only contain Coagulation power parameter. The manner in which the foot pedal representation moves according to foot pedal displacement will be readily understood with reference to FIGS. 12-18.

Referring to FIG. 1, vertical dividers or boundary lines 113-115 extend upwardly from the scale 112, marking the beginning and/or end of a stage of a surgical procedure. The controller representation 110 and boundary lines 113-115 are shown as vertical lines, but may be other shapes and sizes as necessary. In one embodiment of a phacoemulsification surgical system, there are four distinct ranges, positions or stages of foot pedal displacement: 0, 1, 2, and 3. The FIGUREs identify positions, ranges or stages 1-3 before and/or between respective boundary lines 113-115. When a foot pedal is depressed so that it falls within a particular range, the surgical device operates in accordance with the operating parameters and parameter values that are programmed for the particular stage, as reflected on the display screen.

During the initial stage, the foot pedal representation 110 is positioned to the far left and the surgical device is inactive. The foot pedal is depressed so that the foot pedal representation 110 moves from its home position or position 0 to position 1, which is marked by boundary line 113. During Stage 1, irrigation fluid is supplied to the surgical site in accordance with the value (cm $H_2O$) in the irrigation field 120, which can be adjusted using known up/down arrows 122. A source of irrigation can be an elevated bottle or a bag that includes Balanced Salt Solution (BSS) or saline. BSS is delivered to the site by opening a valve allowing the BSS to flow toward the surgical site.

The foot pedal is depressed further so that the foot pedal representation 110 moves from position 1 to position 2 (between boundary lines 113 and 114) in order to initiate aspiration by activating a peristaltic pump. Thus, in this embodiment, irrigation is initiated initially, followed by aspiration. Parameters of the peristaltic pump that can be displayed and controlled include the rotation speed of the pump, which is closely related to the aspiration flow rate, and the maximum vacuum drawn by the pump, current values of which are shown in fields 130 and 131. The current or instantaneous value of vacuum can range from 0 mm Hg to the maximum value mm Hg. When using a peristaltic pump, a vacuum sensor at the pump measures the vacuum and compares the current vacuum level to the vacuum limit. As long as the current vacuum is lower than the vacuum limit, the pump turns at the commanded speed to generate the requested flow. When the current vacuum begins to approach the vacuum limit, the speed of the pump is reduced which, in turn, reduces the flow so that the vacuum does not exceed the vacuum limit.

The foot pedal is depressed further so that the foot pedal representation 110 moves from position 2 to position 3, thereby initiating ultrasound power, after to irrigation and aspiration have commenced. The surgeon manipulates the surgical device so that ultrasound power is delivered to the surgical site. Ultrasound power parameters that can be controlled include the voltage that is provided to the ultrasound handpiece (commonly referred to as ultrasound power), the duration that ultrasound power is activated or the "on time", and the duration that the ultrasound power is de-activated or the "off time". Current values of these power parameters are shown in fields 132-134.

Releasing or raising the foot pedal results in the opposite sequence deactivating ultrasound power, deactivating aspiration, and then deactivating irrigation. The surgeon can activate or de-activate various operating parameters and adjust the parameters as needed during the surgical procedure by periodically or randomly pressing and releasing the foot pedal.

Operating parameters of the surgical device during these stages of the surgical procedure, as controlled by the foot pedal, are dictated by parameter information that is programmed and represented in the graphical user interface 100. More particularly, operating parameters and their minimum and maximum values during each stage of the procedure are displayed on the graphical user interface, extending between the boundary 113-115 lines marking the beginning and/or end of each stage. The amount of irrigation, aspiration and power, and the function of these parameters, can vary with different system configurations and procedures and change as the foot pedal is depressed and released, if the parameters are so programmed.

In the illustrated embodiments, the irrigation flow rate is fixed, as shown in field 120. The manner in which other operating parameters, such as aspiration rate, vacuum level, and ultrasound power, are displayed and adjusted is described below in further detail. Persons skilled in the art will appreciate that the same representation and adjustment techniques can also be applied to irrigation. Persons skilled in the art will appreciate that these or other parameters may be used during other stages of other surgical procedures. Further, although this specification describes irrigation, aspiration, vacuum and power parameters, persons skilled in the art will appreciate that other surgical procedures and other phacoemulsification systems may involve other parameters and, therefore, the exemplary parameters are described in the context of a phacoemulsification procedure, and are not intended to be limiting.

More particularly, as shown in FIG. 1, the interface 100 includes representations of aspiration rate, maximum vacuum level and various power parameters. In the illustrated embodiment, the representation of an operating parameter is a linear representation 140 having two ends 141-142 that terminate at vertical boundary lines. A first or left end 141 represents a minimum value of the parameter, and a second or right end 142 represents a maximum value of the parameter. The ends 141 and 142 can be different values or the same values if the parameter is constant. A line 143 is shown connecting the ends 141 and 142, thus completing the representation of an operating parameter.

For example, in the illustrated embodiment, a representation 150 of aspiration rate extends between boundary lines 113 and 114, as well as 114 and 115, since aspiration is provided during stages 2 and 3, but not stage 1. Similarly, a representation 152 of maximum vacuum pressure 152 also extends between boundary lines 113 and 114, as well as 114 and 115. Power representations include representations of on time, off time and a power function, shown as 155, 156 and 157, respectively. Ends 153 and 154 of a power representation terminate at boundary lines 114 and 115, thus indicating the minimum and maximum value of the power parameter.

The ends of representations include fields or boxes, which indicate the minimum and maximum parameter values at the boundary lines at the beginning and/or end of a stage. For example, in the embodiment shown in FIG. 1, at the beginning of stage 2 at boundary line 114, the maximum value of the vacuum, 80 mm Hg, is indicated in field 160, and the value of the rate of aspiration is 23 cc/min is indicated in field 161. Similar fields are provided to indicate the minimum and maximum value of power parameters.

In the illustrated embodiment shown in FIG. 1, the power parameter values are selected to provide continuous power, since the off time representation 156 extends between two "0" values. In other words, the power is off for "0" time, i.e., power is on all of the time and is, therefore, continuous. In this continuous power example, the on time representation 155 is constant or fixed at 35 ms. Since the power is continuous, any non-zero "on time" value can be used. Thus, other selections besides 35 ms can be used. The power function representation 157 indicates that continuous ultrasound power increases linearly between a minimum value of 0% and 40% of the maximum available power, as the foot pedal is moved through the third stage. In other words, the continuous power increases as the foot pedal is depressed further into the third stage, up to a maximum of 40% of available power.

In addition to these aspiration, vacuum and power representations, there are also separate fields or boxes that indicate instantaneous power 132, on time 133, off time 134, vacuum 131, and aspiration rate 130 at a particular foot pedal position. All of these fields are shown as "0" since, for purposes of describing the parameter representations, the foot pedal is maintained in its home position.

Figure 2:
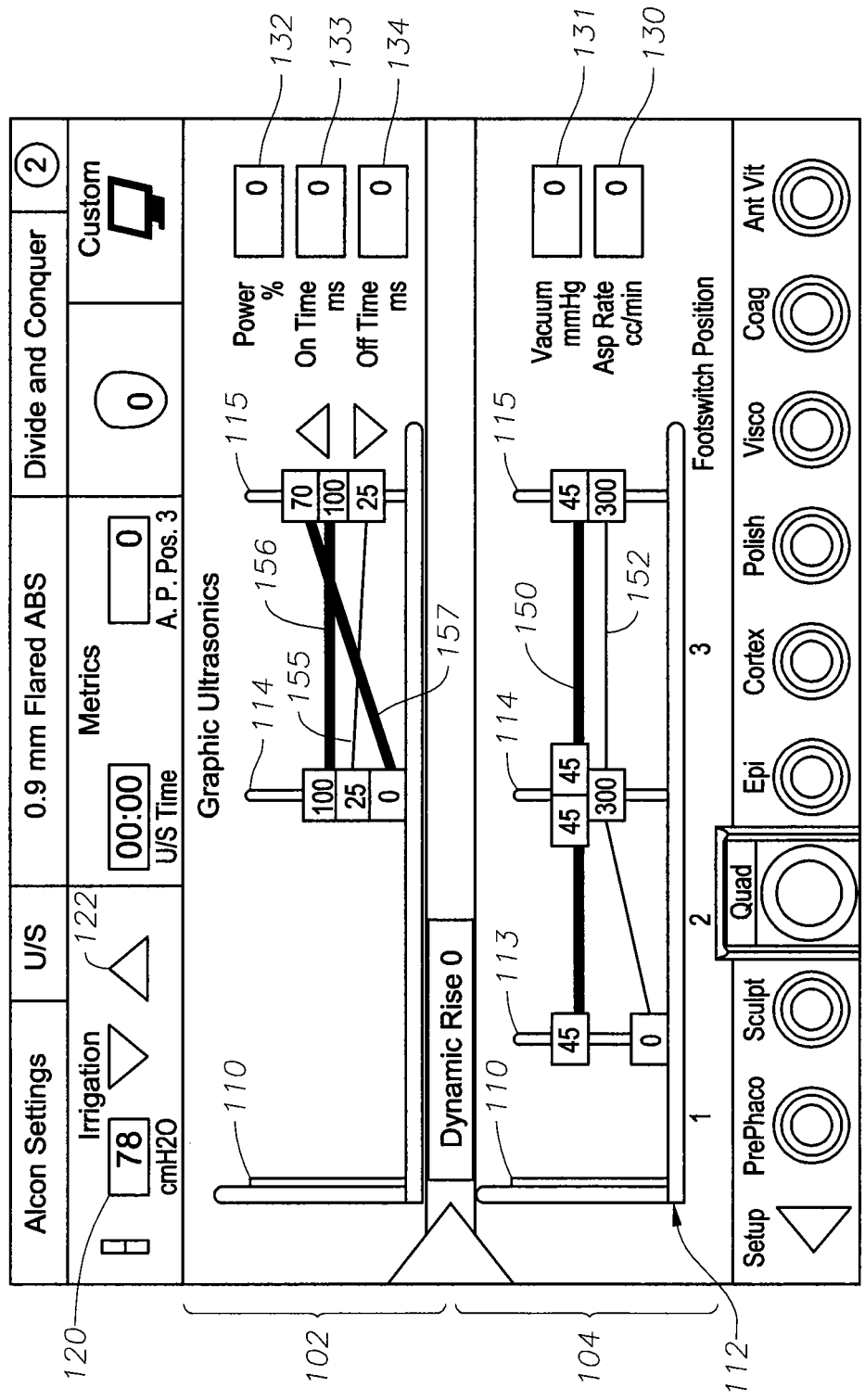
FIG. 2 illustrates a graphical user interface according to one embodiment that includes representations of parameters that are selected to provide pulsed ultrasound power that varies linearly.

Referring to FIG. 2, representations of parameters are adjusted to provide for other parameter values, operating modes and control over the surgical device. As shown in FIG. 1, the position of the foot pedal representation remains at its initial position in order to describe and illustrate the parameter settings and adjustments. In FIG. 1, the parameter representations are configured to provide continuous power that varies linearly. In FIG. 2, adjustments to parameters provide pulsed power that varies linearly. The ultrasound power 157 now increases linearly from 0% to 70%. Thus, the maximum or end value 154 of the power was increased from 40% to 70%. The aspiration flow rate 150 was increased from 23 cc/min to 45 cc/min for stages 2 and 3, and the maximum vacuum 152, which was previously constant at 80 mm Hg, now varies linearly during stage 2 between 0 and 300 mmHg, and is constant during stage 3 at 300 mm Hg.

The ultrasound "on time" 155 was reduced from 35 ms to 25 ms, and the ultrasound off time 156 is now a constant 100 ms, whereas in FIG. 1, the off time 156 was "0" (indicating that power was always on or was continuous). Thus, as shown in FIG. 2, for each pulse cycle of 125 ms, ultrasound is on for 25 ms, and off for 100 ms, providing 8 pulses per second. The ratio of the ultrasound on time 155 to the total cycle time is 25/125=0.2, or a duty cycle of 20%. The duty cycle can be adjusted by adjusting the ultrasound on time 155 and/or the off time 156.

Figure 3:
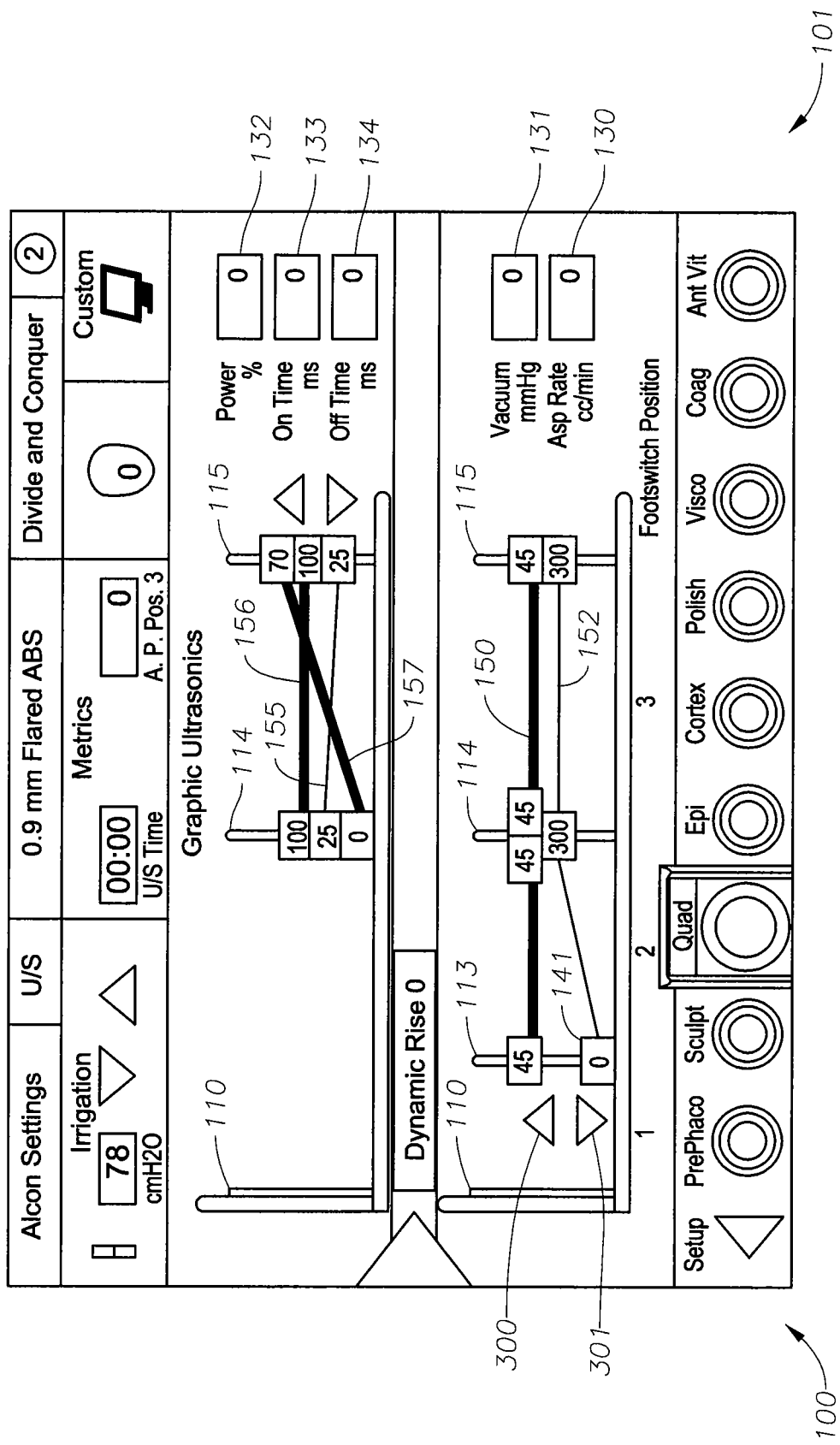
FIG. 3 illustrates a graphical user interface according to one embodiment that includes representations of parameters that are selected to provide pulsed ultrasound power and illustrates one manner in which values of parameter representations can be adjusted.
Figure 4:
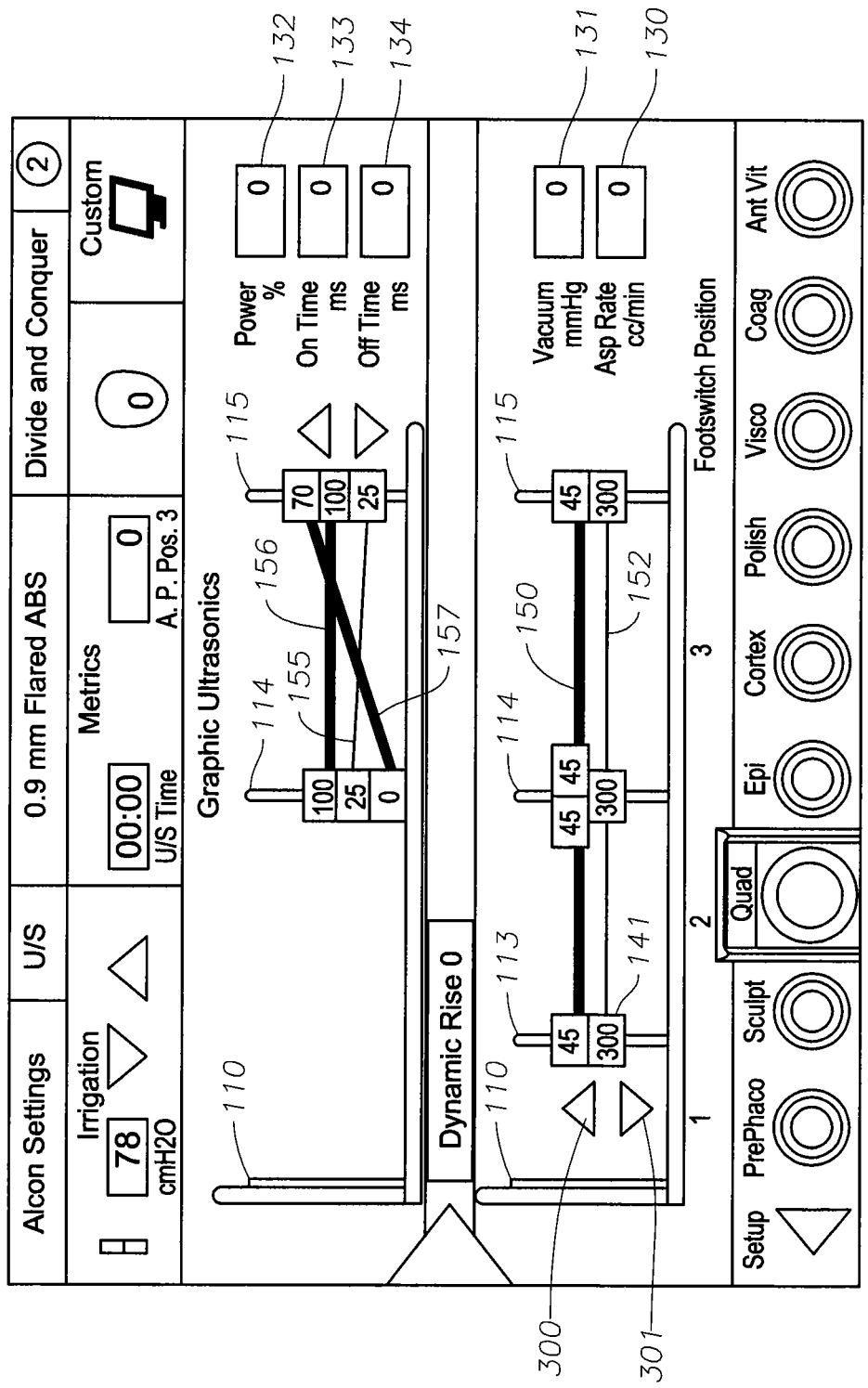
FIG. 4 further illustrates how the values of parameter representations can be adjusted.
Figure 5:
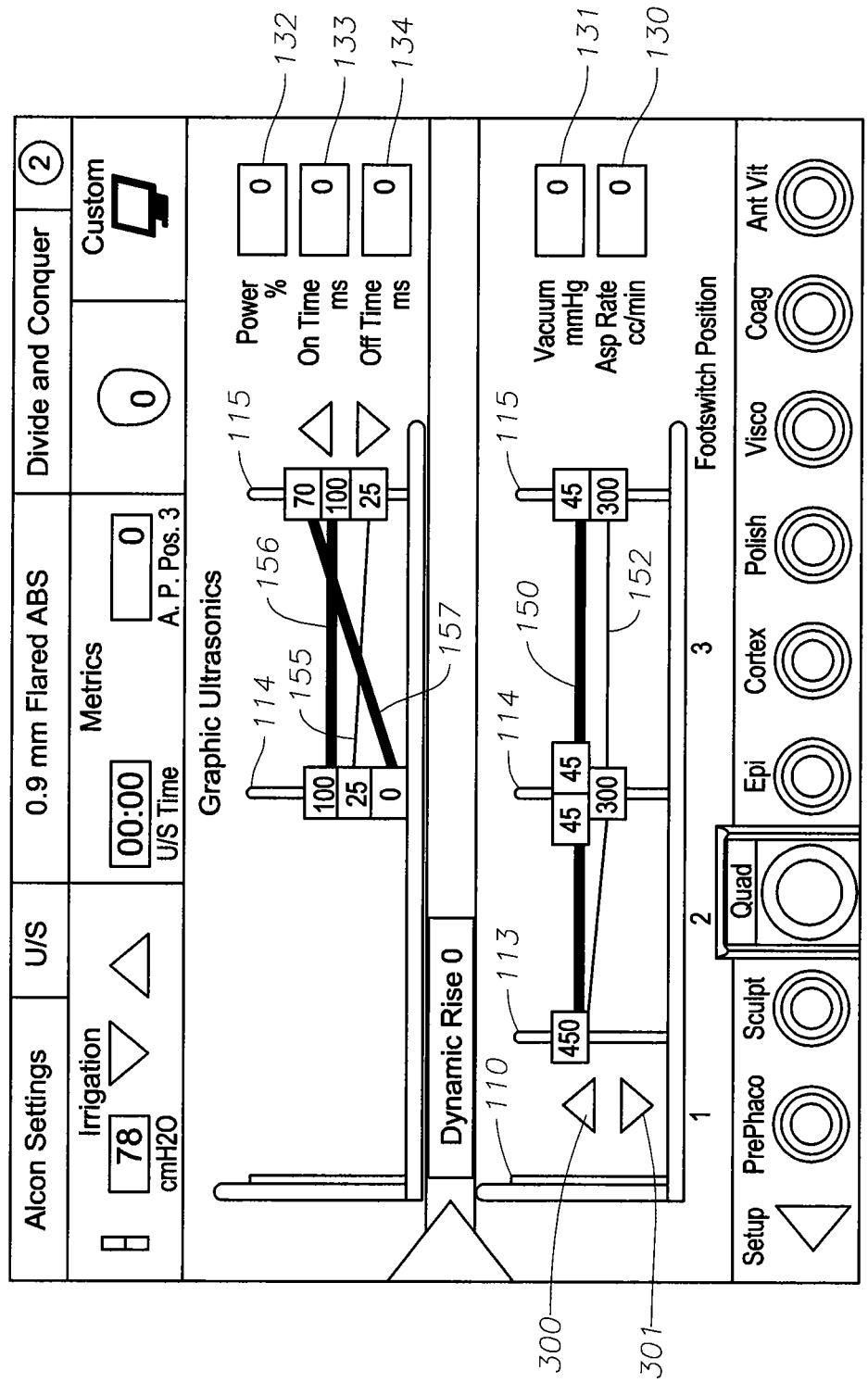
FIG. 5 illustrates a graphical user interface and how overlapping representations of parameters can be displayed by switching between displayed representations.
Figure 6:
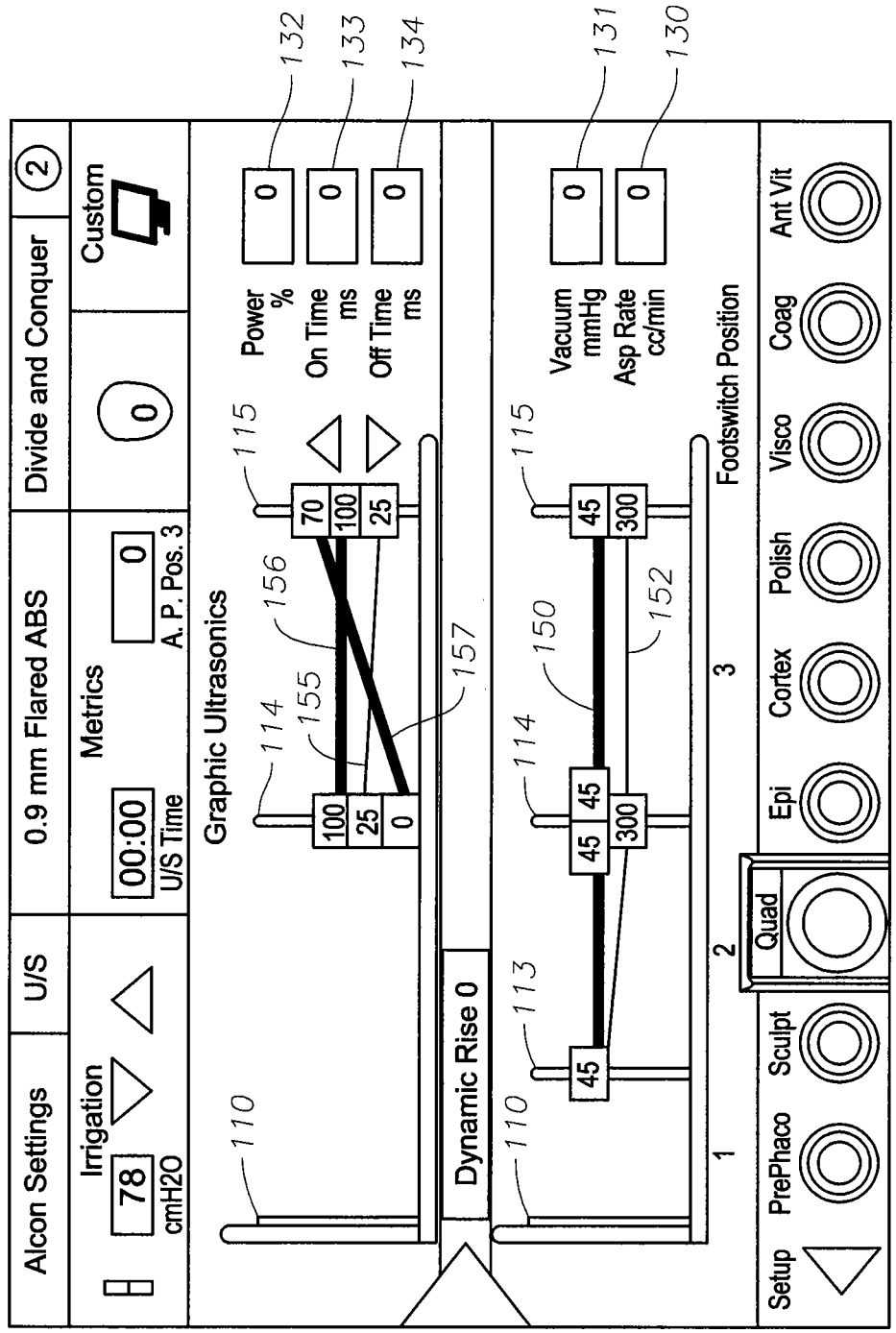
FIG. 6 further illustrates how overlapping representations of parameters can be displayed.

Parameter representations and their values can be changed in various ways. An example is shown in FIGS. 3 and 4 with reference to changing the maximum vacuum level 152. In this embodiment, illustrating changing the maximum vacuum level at the beginning of stage 2, the surgeon contacts a first end 141 of the vacuum representation 152, e.g., by touch, with a stylus or pencil, e.g., as used with a Personal Digital Assistant (PDA) or other similar device to activate, select or highlight the first end 141. The contacted end 141 is moved from a first or initial location on the display screen 101 to a second location on the display screen 101. This can be performed, for example, by dragging a finger along the display screen 101 to move the first end 141 of the vacuum representation 152. Thus, moving an end of a representation can be similar to a similar "click and drag" function of a mouse. Alternatively, an end can be contacted, and the surgeon can lift his or her finger and contact the new location on the display screen.

In the illustrated embodiment, in which vertical boundary lines divide the stages of a phacoemulsification procedure, the surgeon can select an end of a representation and move or drag it along the vertical boundary lines to increase or decrease the starting or end values of a parameter. For example, the surgeon can contact the first or left end 141 of the vacuum representation 152, indicating the minimum or starting value, and drag or move the left end 141 to a new location on the vertical divider 113 to change the value from "0" to a new, higher or intermediate, non-zero value.

In another embodiment, after the surgeon contacts the first end 141, thus selecting or activating the first end 141, the surgeon can use the up/down arrows 300 and 301 to change the initial value of maximum vacuum 152 and move the first end 141 of the representation. In the illustrated embodiment, shown in FIG. 3, only the "up" arrow 300 is activated since the initial vacuum level in this example is "0" and cannot be reduced, thus disabling the down arrow 301. Of course, if the initial vacuum level were a non-zero level, both arrows 300 and 301 would be active to allow them to increase or decrease the maximum vacuum level. After pressing the up arrow 300, the surgeon selects the new maximum vacuum level at the beginning of stage 2 to be 300 mm Hg, as shown in FIG. 4.

In some cases, different parameter representations may overlap, thus covering a portion or all of an end of the representation that includes a value. Overlapping may result from the parameters as originally selected or due to re-positioning portions of a parameter. For example, referring to FIG. 5, the first end 141 or field of the vacuum representation 152 (450 mm Hg) overlaps the first end or field of the aspiration rate representation 150 (45 cc/min.) The end of the representation that is shown above the other can be switched or toggled by clicking or touching another portion the corresponding representation. Thus, referring to FIGS. 5 and 6, the aspiration rate representation 150 is selected so that the value of 45 cc/min is visible over the underlying 450 mm Hg vacuum value.

Figure 7:
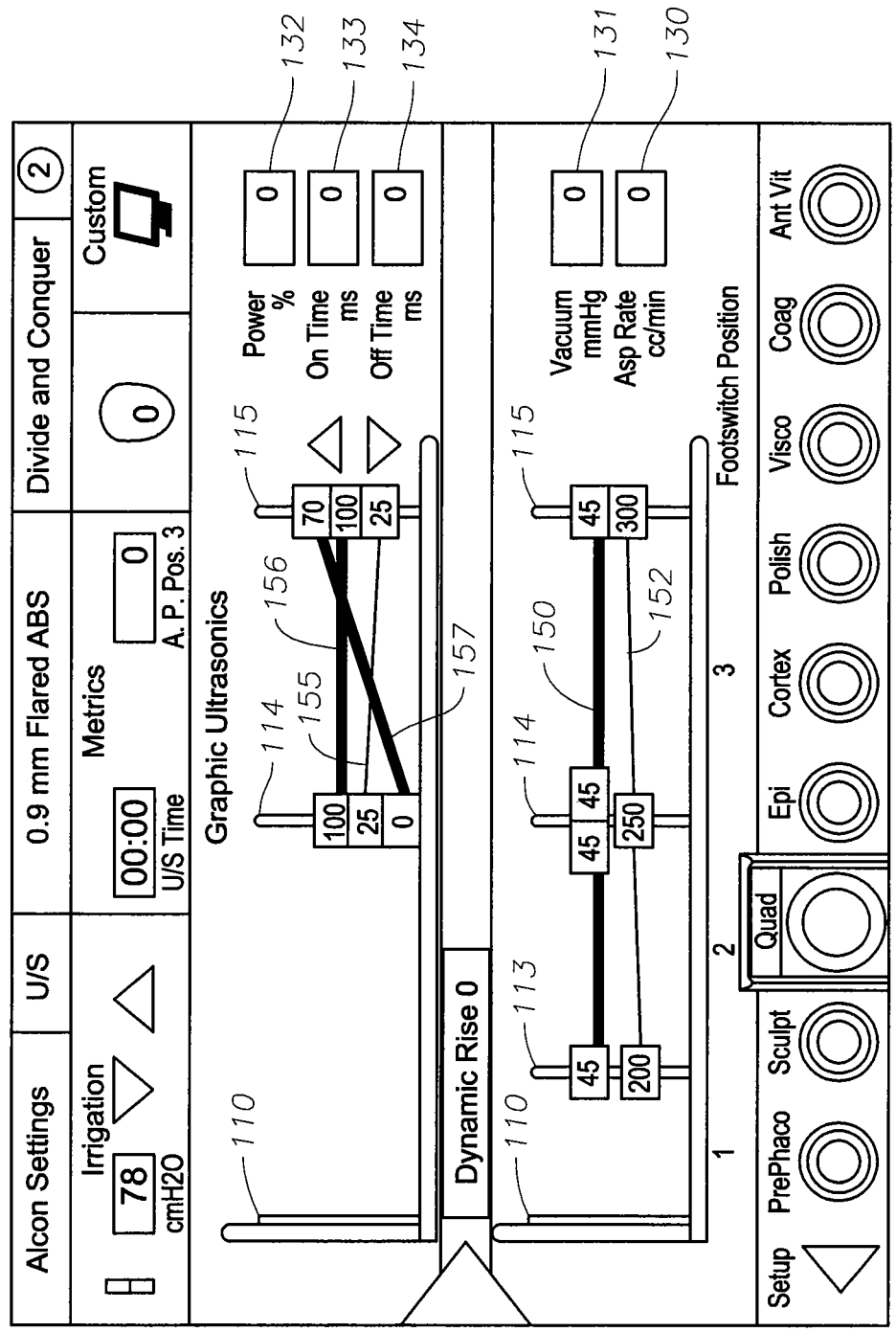
FIG. 7 illustrates a graphical user interface that includes a representation of vacuum that continuously increases throughout multiple foot pedal positions or stages.

Referring to FIG. 7, graphical user interfaces can be configured with representations that allow for a parameter to increase continuously throughout position 2 and also throughout position 3. In the illustrated embodiment, the maximum vacuum level 152 is represented as increasing from 200 mm Hg to 250 mm Hg in position 2, and increases from 250 mm Hg to 300 mmHg in position 3. The ability to provide these types of customized controls can be particularly useful to provide increased cooling as more and more ultrasound is applied. This type of control may also reduce the possibility of instances of excessive ultrasound power with insufficient irrigation and aspiration, thus causing thermal injury to the eye tissues.

Figure 8:
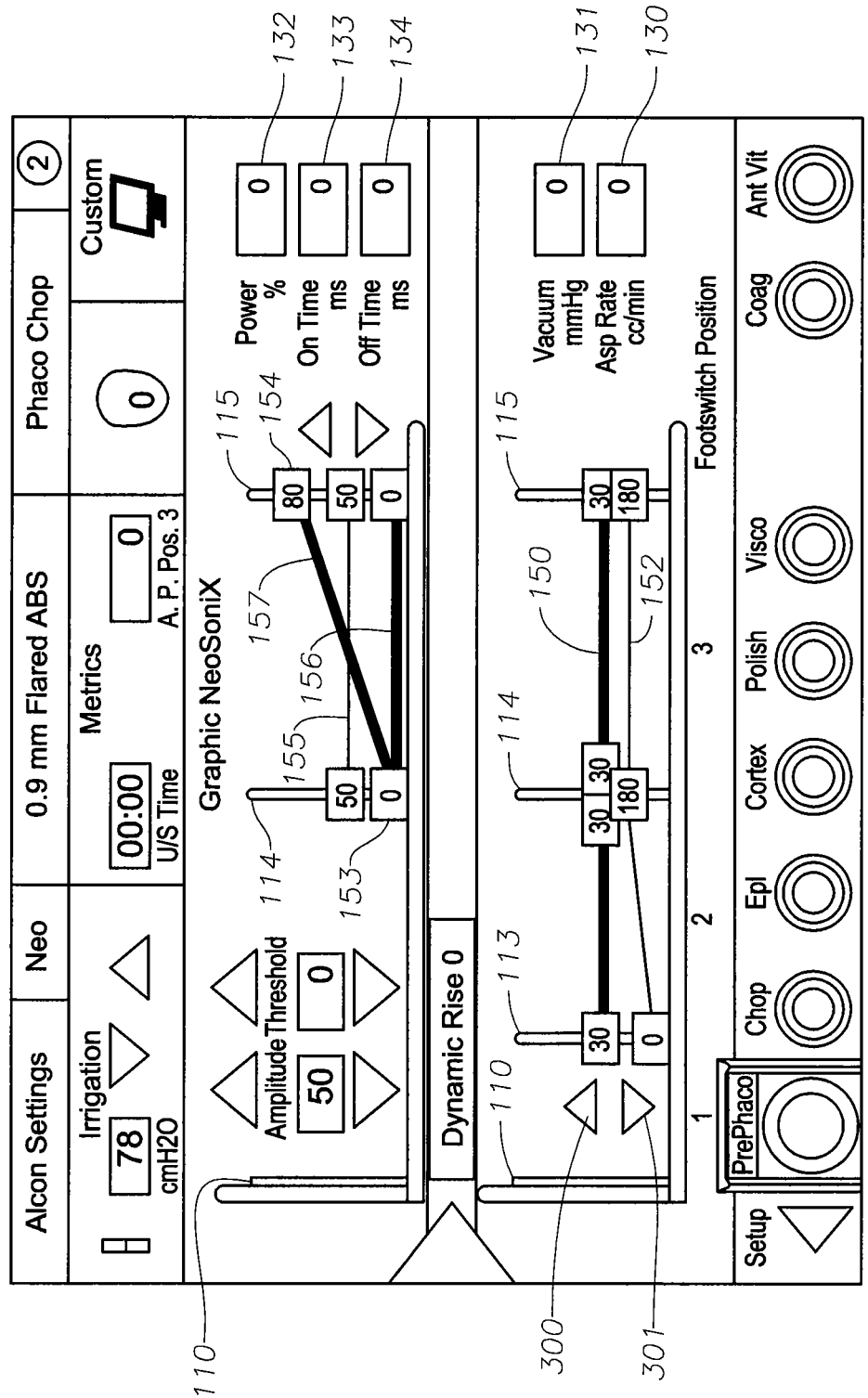
FIG. 8 illustrates a graphical user interface according to another embodiment that includes representations of parameters that are selected to provide continuous ultrasound power that varies linearly.

FIGS. 8-11 illustrate further embodiments and show how representations of various surgical parameters can be adjusted to customize control of surgical devices. Referring to FIG. 8, the graphical user interface is configured in a manner that is similar to the interface shown in FIG. 1 with certain differences. The interface includes representations of aspiration rate 150, maximum vacuum level 152 and various power parameters. At the beginning of stage 2, at boundary line 113, the value of the vacuum is 0 mm Hg and linearly increases to 180 mm Hg, and is then constant at 180 mm Hg through stage 3. Additionally, the aspiration level 150 is at 30, and the power linearly increases from 0 to 80%.

Figure 9:
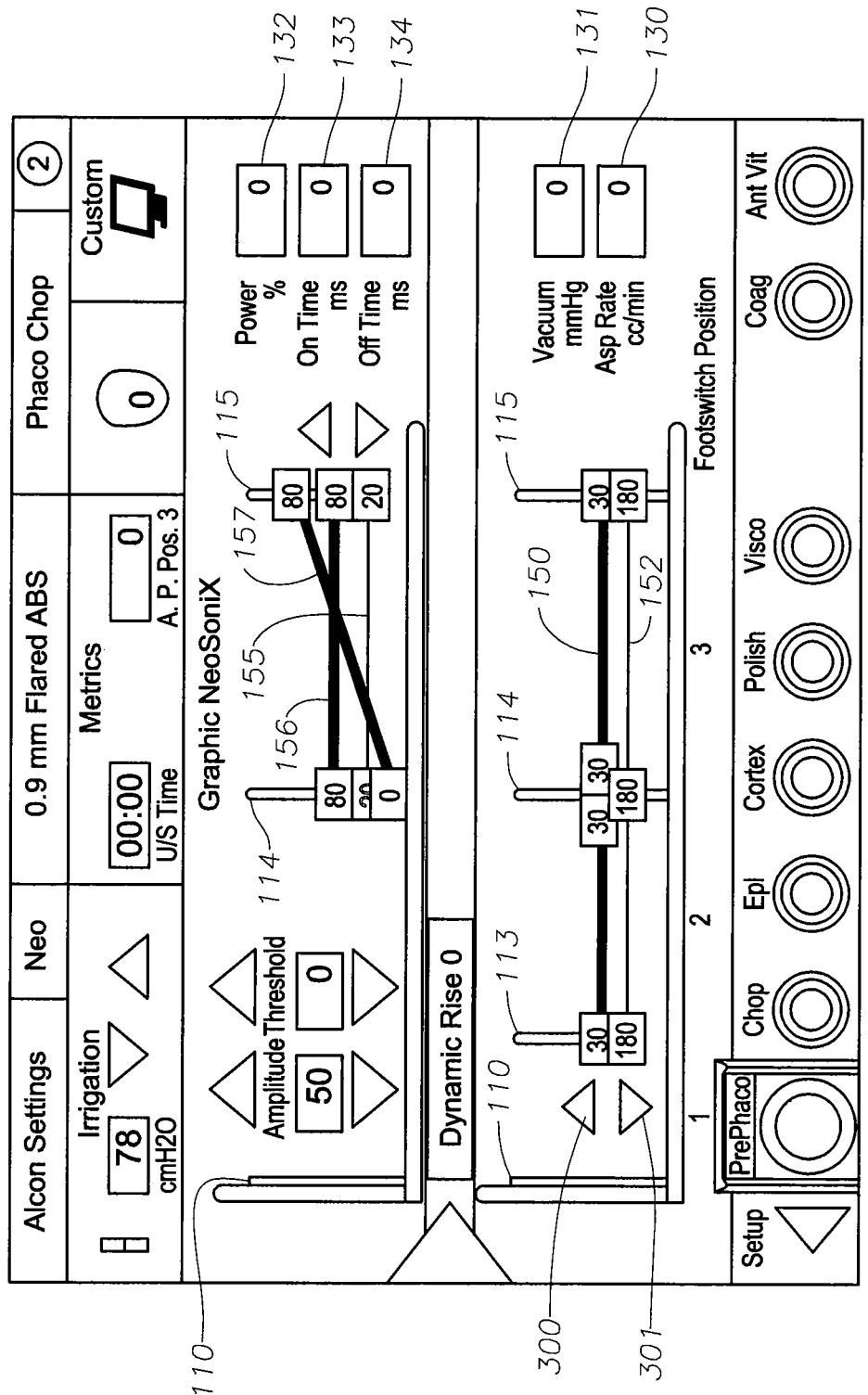
FIG. 9 illustrates a graphical user interface according to another embodiment that includes parameter representations that are selected to provide pulsed ultrasound power that varies linearly.

FIG. 9 illustrates a graphical user interface that includes parameter representations configured to promote and control pulsed ultrasound power that varies linearly, similar to the interface shown in FIG. 2. As shown in FIG. 9, the aspiration flow rate 150 is constant throughout stages 2 and 3 at 30 cc/min, whereas in FIG. 2, the aspiration flow rate increased from 0-300 cc/min during stage 2, and was then constant at 300 c/min during stage 3. Ultrasound power 157 now increases linearly from 0% to 80% during stage 3, the "on time" 155 is 20 ms, and the ultrasound off time 156 is now a constant 80 ms rather than 100 ms, as shown in FIG. 2. With this configuration, for each pulse cycle of 100 ms, ultrasound is on for 20 ms, and off for 80 ms, and the duty cycle is 20%, as in FIG. 2, but this configuration provides 10 pulses per second, whereas the controls shown in FIG. 2 provide 8 pulses per second. The controls can be adjusted, as necessary, by moving ends of the ultrasound on time 155 and/or the ends of the ultrasound off time 156 representations, as previously described.

Figure 10:
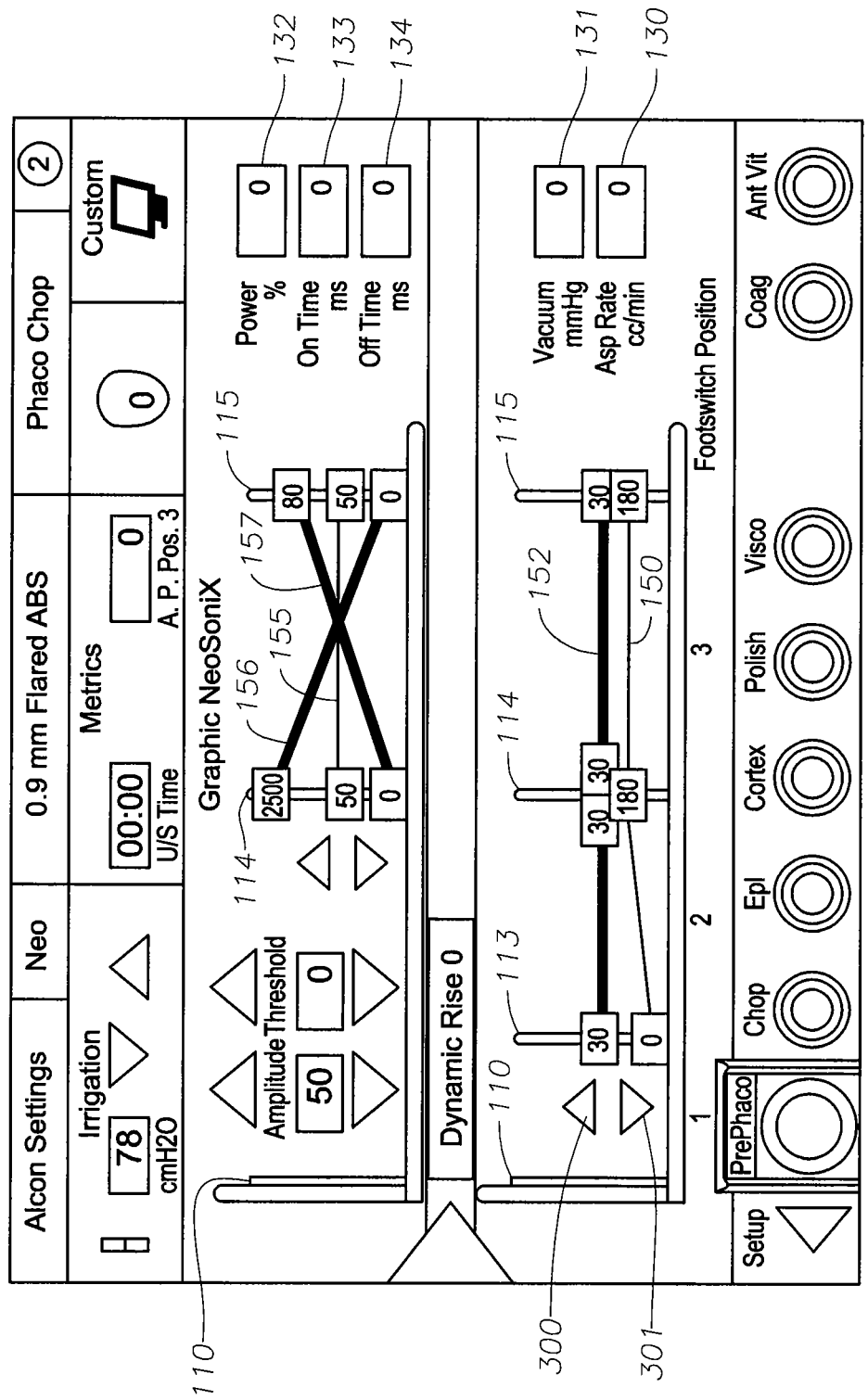
FIG. 10 illustrates a graphical user interface according to a further embodiment that includes representations that are selected to provide burst ultrasound power that varies linearly.

Referring to FIG. 10, a graphical user interface is shown that includes parameter representations that provide controls for linear burst ultrasound. In this arrangement, the aspiration flow rate 150 is constant throughout stages 2 and 3 at 30 cc/min, and increases from 0-180 cc/min during stage 2, and is then constant at 180 c/min during stage 3. Ultrasound power now 157 increases linearly from 0% to 80% during stage 3. The on-time 155 is a constant 50 ms. The off time 156, however, decreases linearly from 2500 ms to 0 as the foot pedal moves through stage 3. The result of these control parameters is that when the foot pedal is pushed all the way down, i.e., at the end of stage 3, the ultrasound power is continuous.

Figure 11:
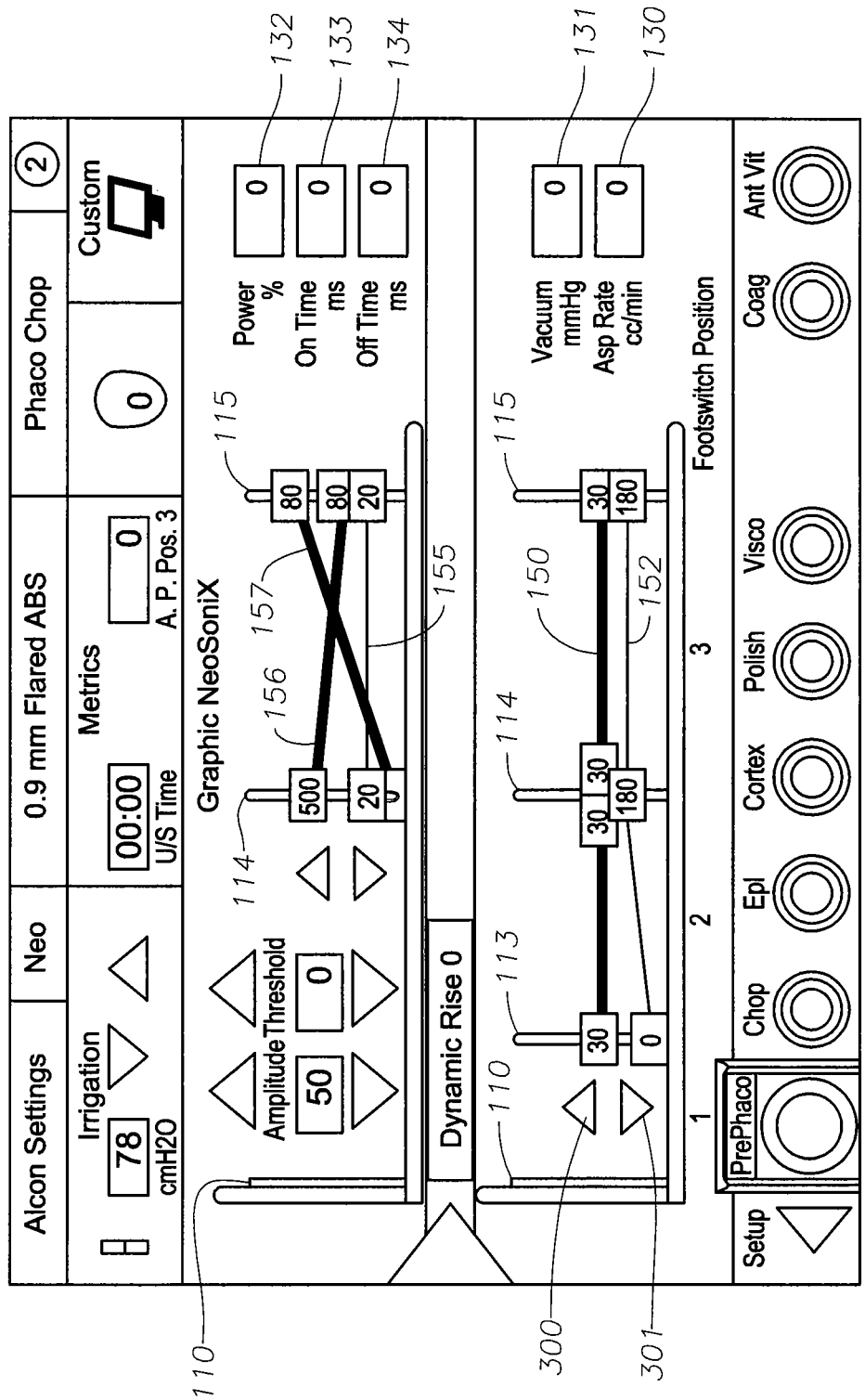
FIG. 11 illustrates a graphical user interface according to further embodiment that includes parameter representations that are set to provide modified burst ultrasound power.

FIG. 11 illustrates yet a further graphical user interface including representations of operating parameters that are configured to provide modified burst ultrasound power. In this interface, the aspiration flow rate 150 and maximum vacuum levels 152 are the same as shown in FIG. 10. The power 157 also linearly increases from 0 to 80% as shown in FIG. 10. The on-time 155, however, is fixed at 20 ms rather than 50 ms, and the off time 156 decreases linearly from 500 ms to 80 ms through stage 3. As a result, when the foot pedal is pushed all the way down, the power is not continuous as the controls shown in FIG. 10 would provide. Rather, the ultrasound power is at 80% with an off time of 80 ms and an on time of 20 ms, for a duty cycle of 20%.

FIGS. 12-18 illustrate how the parameter representations and the adjustments to the same, are used to control a surgical device as a foot pedal is pressed to different positions. Beginning with FIG. 12, the interface is similar to the interface shown in FIG. 2 and includes an aspiration flow 150 rate that increases from 20 cc/min to 45 cc/min during the second stage, and then remains fixed at 45 cc/min for the third stage. Maximum vacuum 152 linearly increases during stage 2 between 0 and 300 mmHg, and is constant during stage 3 at 300 mm Hg, as in FIG. 2. Ultrasound power 157 increases linearly from 0% to 70% during stage 3, the "on time" 155 is 25 ms, and the off time 156 is 100 ms, also as shown in FIG. 2.

Figure 12:
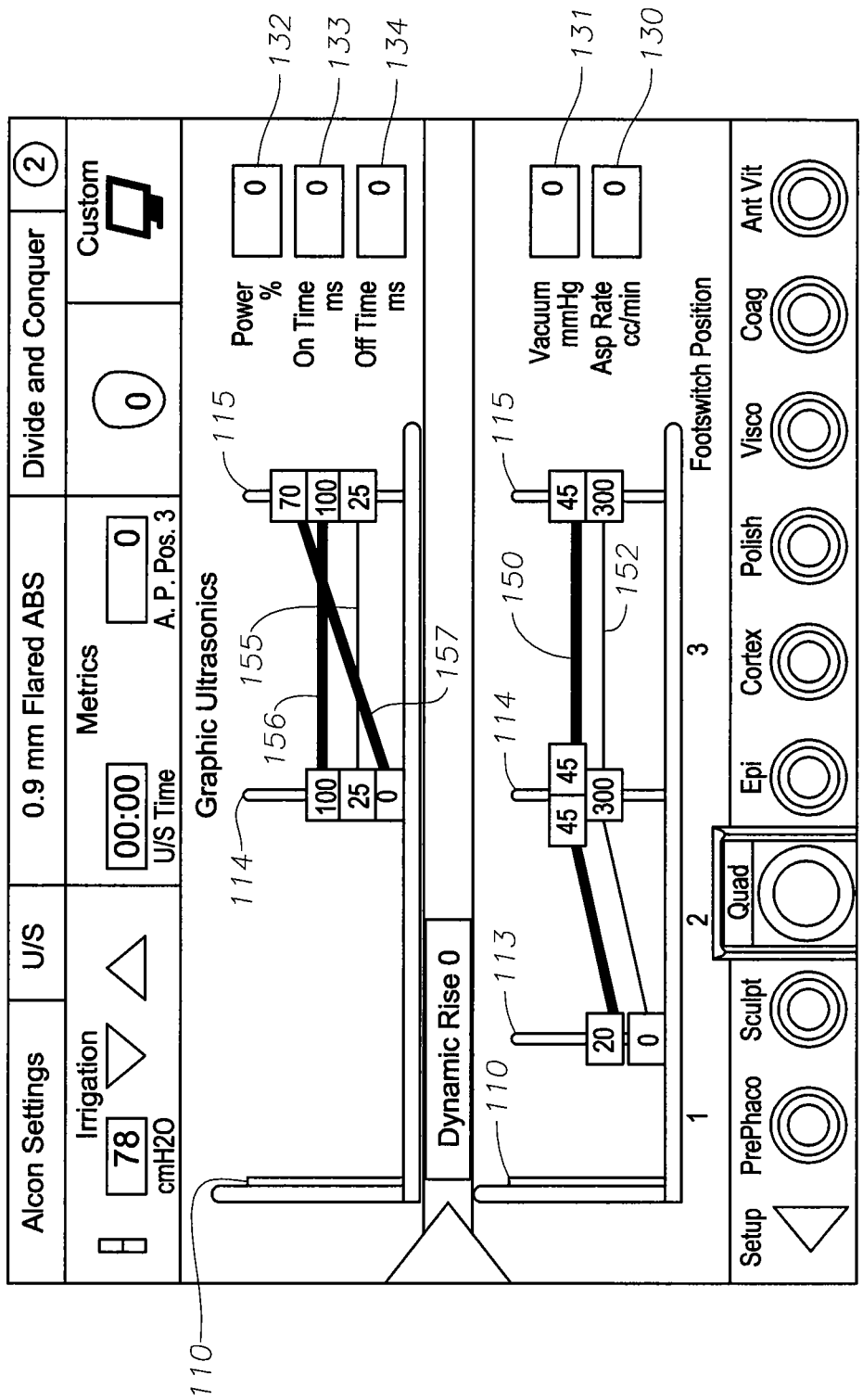
FIG. 12 illustrates representations of surgical device parameters relative to a initial position of a representation of a foot pedal and the corresponding current values of the parameters invoked by the foot pedal position.

As shown in FIG. 12, the foot pedal representation 110 is initially at Position 0, e.g., when the foot pedal is not depressed. Thus, the surgical device is inactive, and there is no irrigation, aspiration or ultrasound power. FIG. 12 shows each of the instantaneous power 132, on time 133, off time 134, vacuum 131 and aspiration rate 130 as "0" since the surgical device is inactive.

Figure 13:
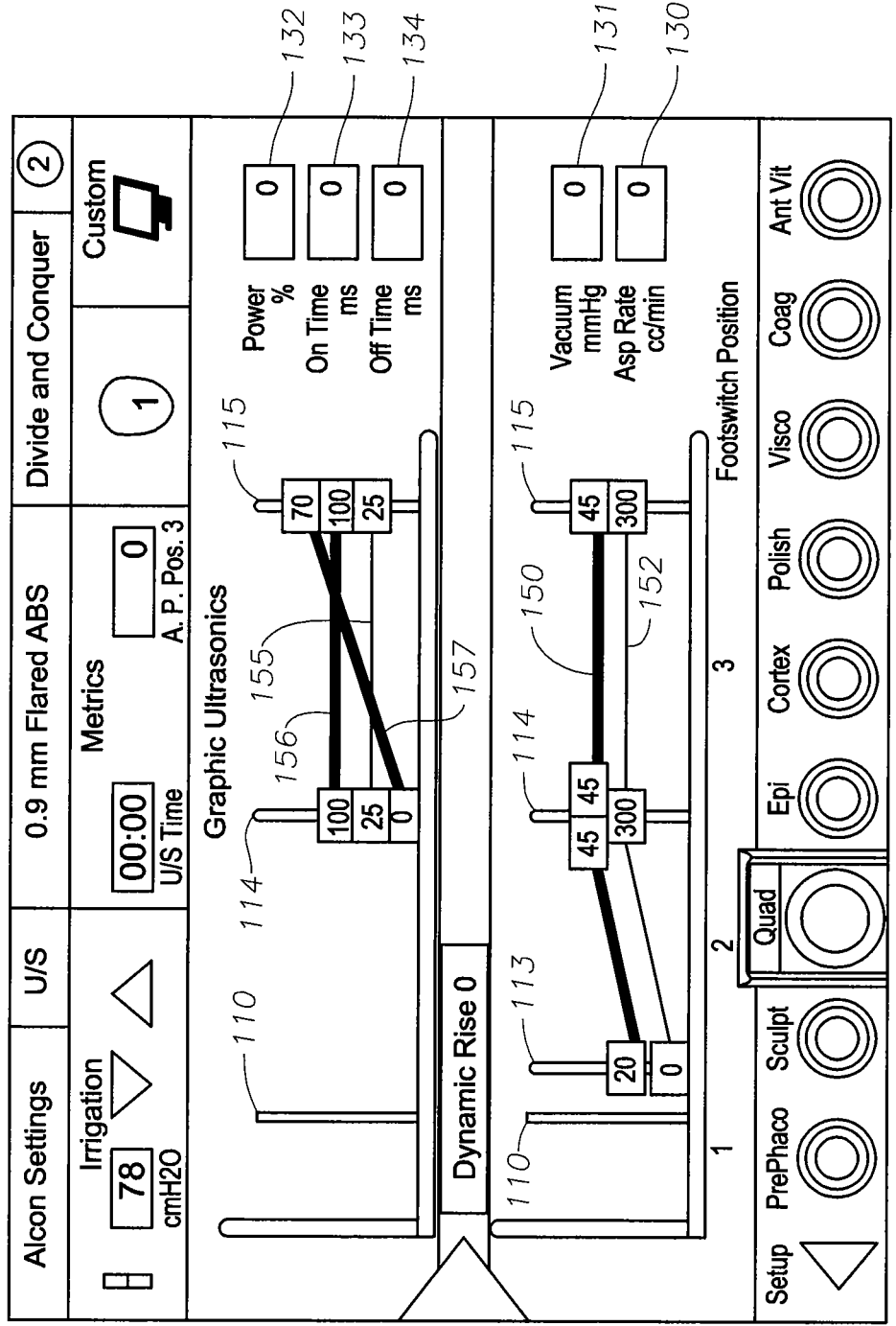
FIG. 13 illustrates representations of surgical device parameters relative to a representation of a foot pedal positioned in a first stage or range of positions, and the corresponding current values of the parameters invoked by the foot pedal position.

As the surgeon presses down on the foot pedal, the foot pedal and the foot pedal representation 110 move into position or stage 1, as shown in FIG. 13, during which irrigation fluid is provided to the surgical site at 78 cm H$_2$O. Since there is only irrigation at this stage, the instantaneous power 132, on time 133, off time 134, vacuum 131 and aspiration rate 130 values remain "0".

Figure 14:
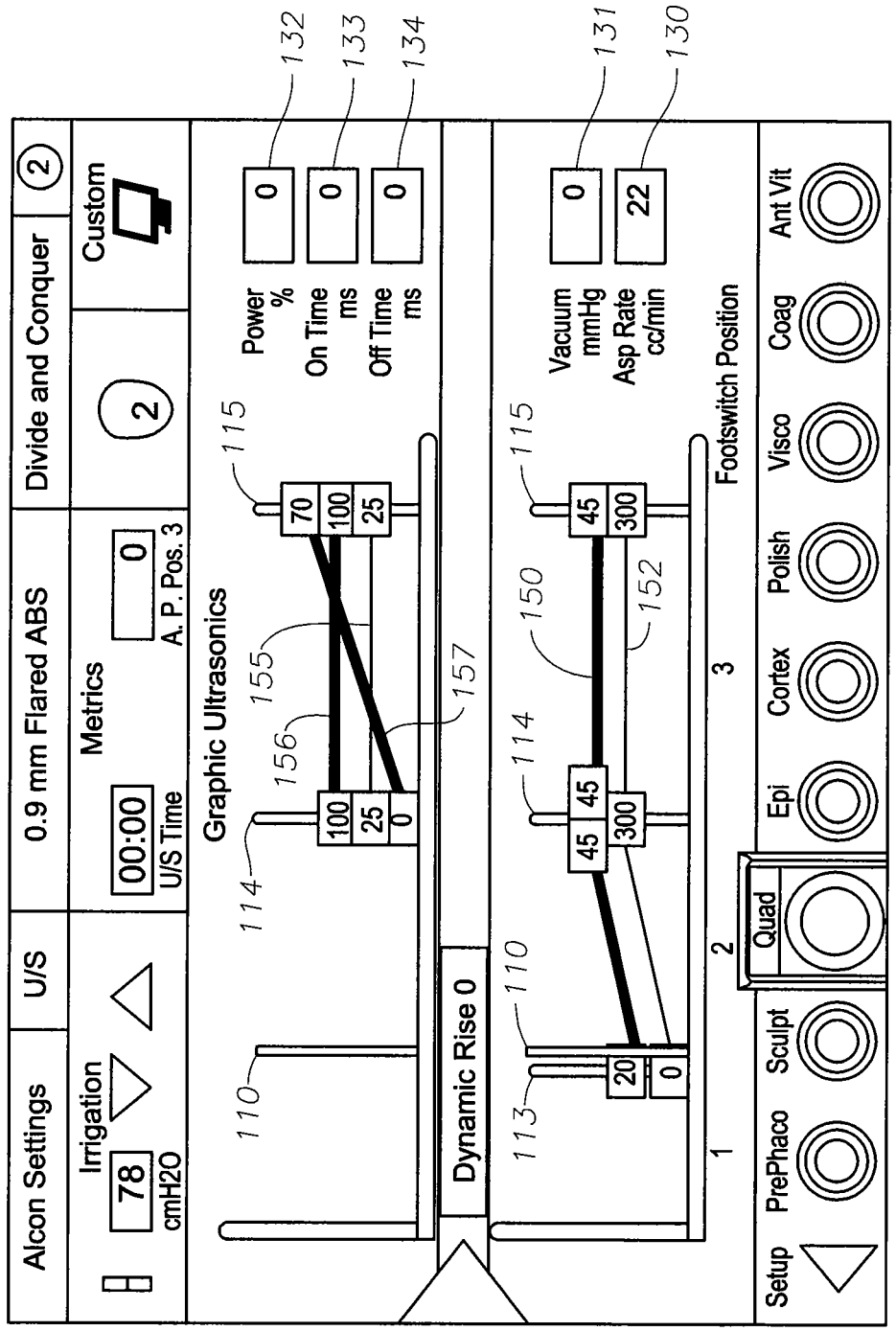
FIG. 14 illustrates representations of surgical device parameters relative to a representation of a foot pedal positioned within a second stage or range of positions and the corresponding current values of the parameters invoked by the foot pedal position.
Figure 15:
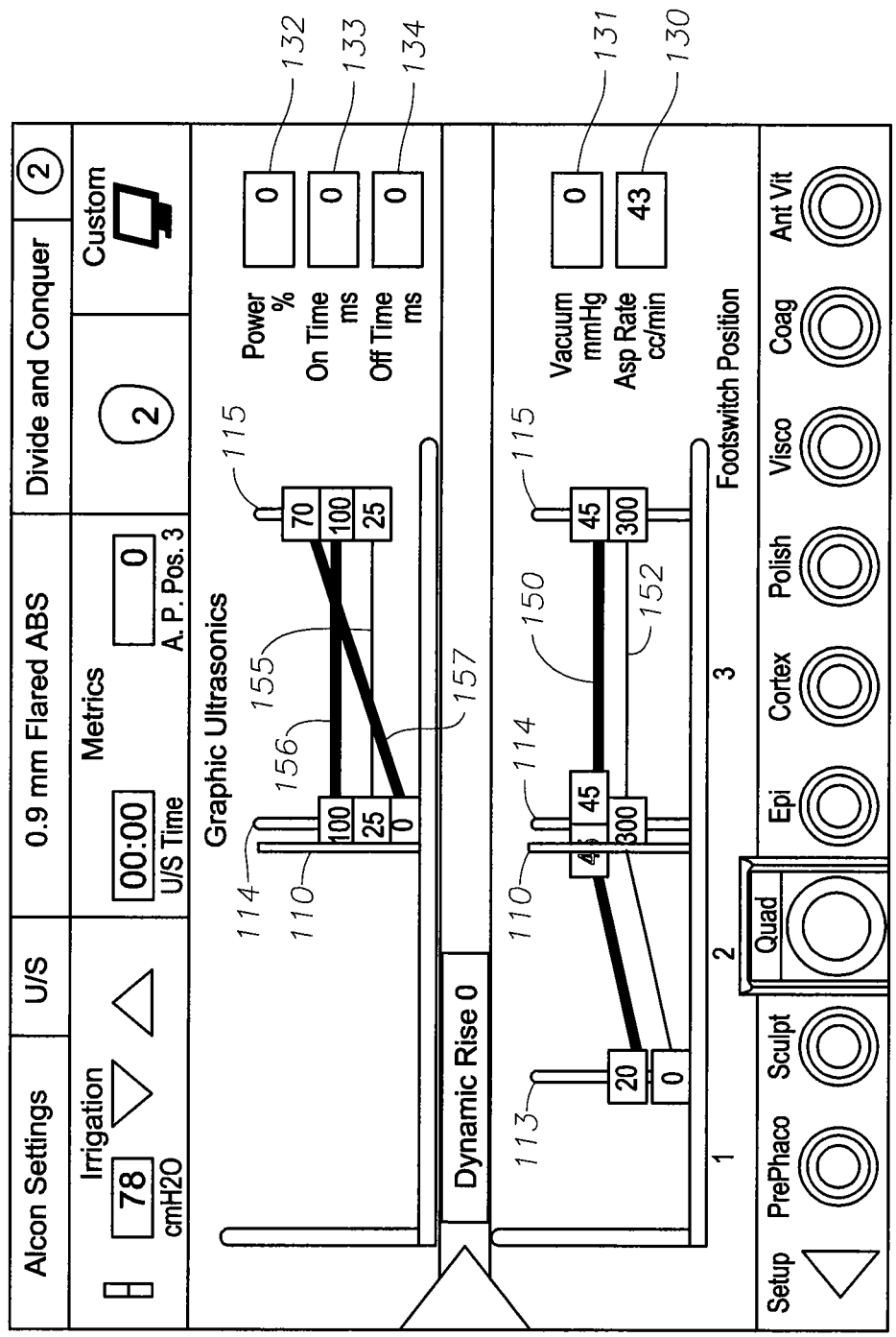
FIG. 15 illustrates representations of surgical device parameters relative to a representation of a foot pedal positioned further within a second stage or range of positions and the corresponding current values of the parameters invoked by the foot pedal position.

Referring to FIG. 14, pressing the foot pedal further moves the foot pedal and the foot pedal representations 110 from position or stage 1 to position or stage 2, between boundary lines 113 and 114. During this stage, aspiration is commenced. The vacuum limit 152 linearly increases from 20 mmHg to a value not exceeding 45 mmHg, and the aspiration rate 150 linearly increases from 0 cc/min to 300 cc/min. The instantaneous aspiration rate 130 reflects this and shows the aspiration rate for a particular foot pedal position being 22 cc/min. The instantaneous vacuum 131 is shown as 0 mm Hg and can range from 0 mm Hg to the maximum vacuum level which, in this example, is 300 mm Hg. Referring to FIG. 15, as the foot pedal is depressed further, and the foot pedal representations 110 approaches the boundary line 114, the aspiration rate 150 linearly increases, as reflected by the instantaneous aspiration rate 130 showing 43 cc/min.

Figure 16:
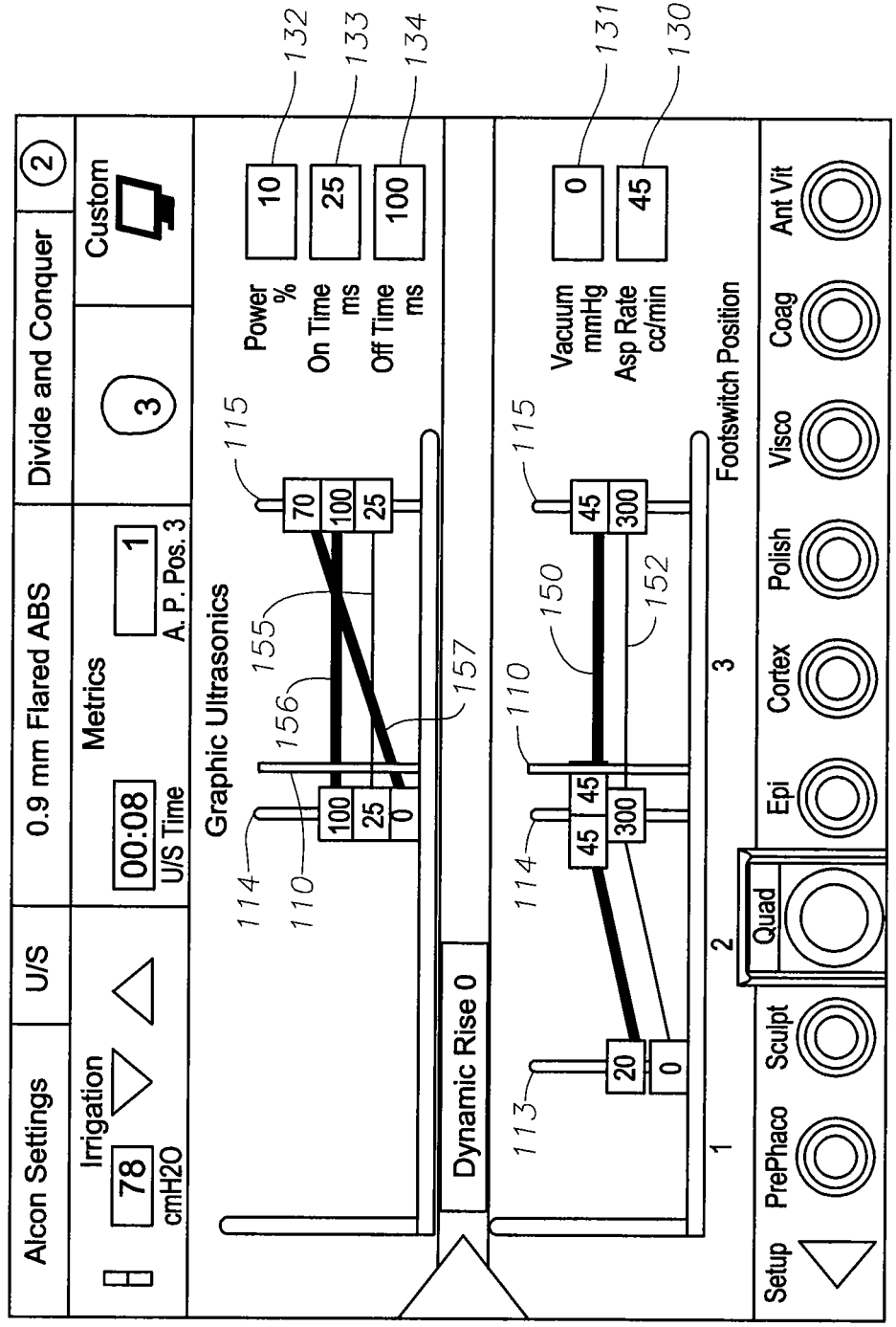
FIG. 16 illustrates representations of surgical device parameters relative to a representation of a foot pedal positioned within a third stage or range of positions and the corresponding current values of the parameters invoked by the foot pedal position.

Referring to FIG. 16, the foot pedal is pressed further so that the foot pedal and the representation 110 cross the boundary line 114 and enter the third stage or position, between boundary lines 114 and 115. As the foot pedal cross over into the third position, the aspiration rate 150 and vacuum 152 are constant, and ultrasound power 157 is commenced, as reflected in the instantaneous fields 132, 133, 134, 131 and 130 indicating 10% power, 25% on time, 100% off time, 0 mm Hg vacuum and an aspiration rate of 44 cc/min, respectively.

Figure 17:
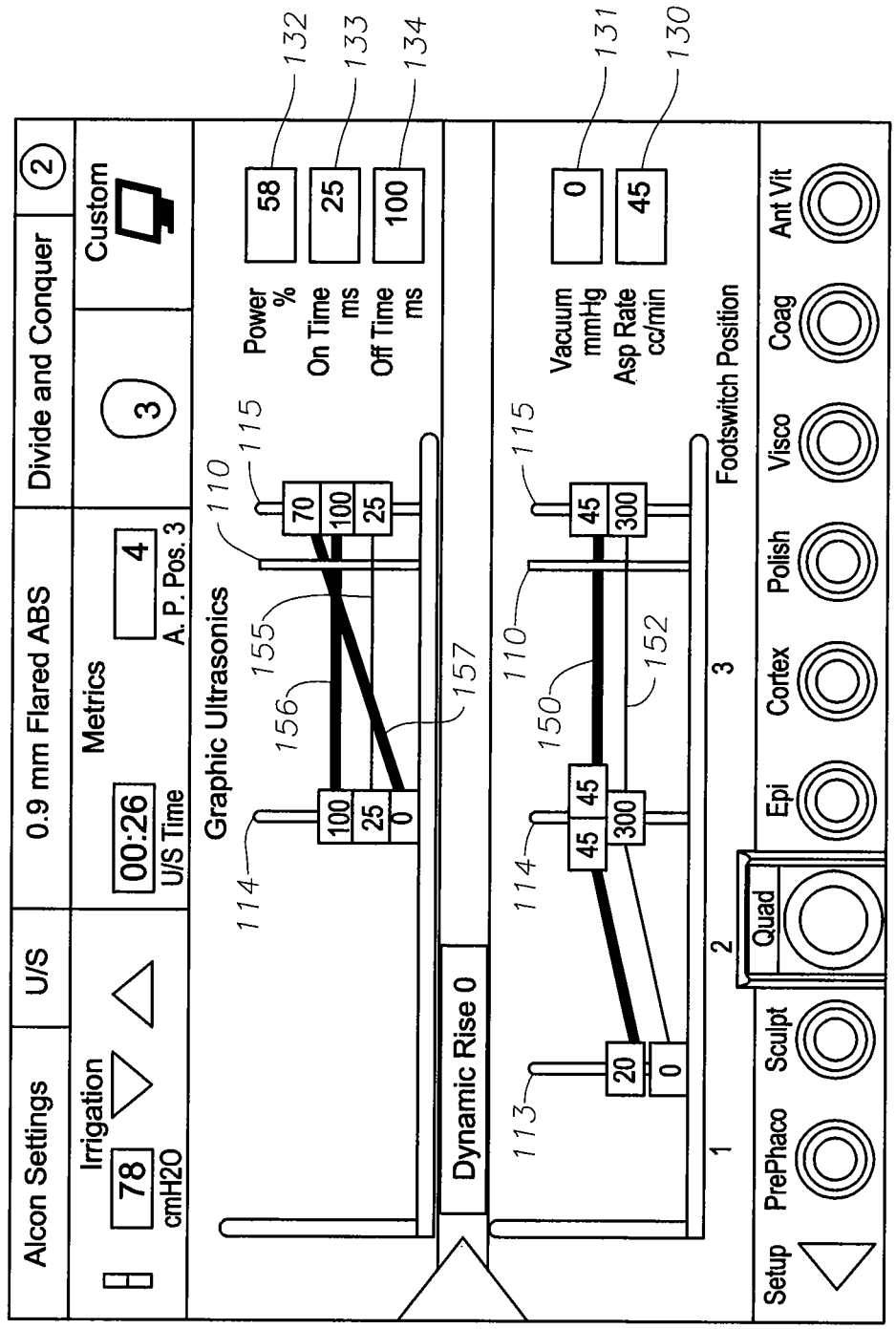
FIG. 17 illustrates representations of surgical device parameters relative to a representation of a foot pedal positioned further within a third stage or range of positions and the corresponding current values of the parameters invoked by the foot pedal position.
Figure 18:
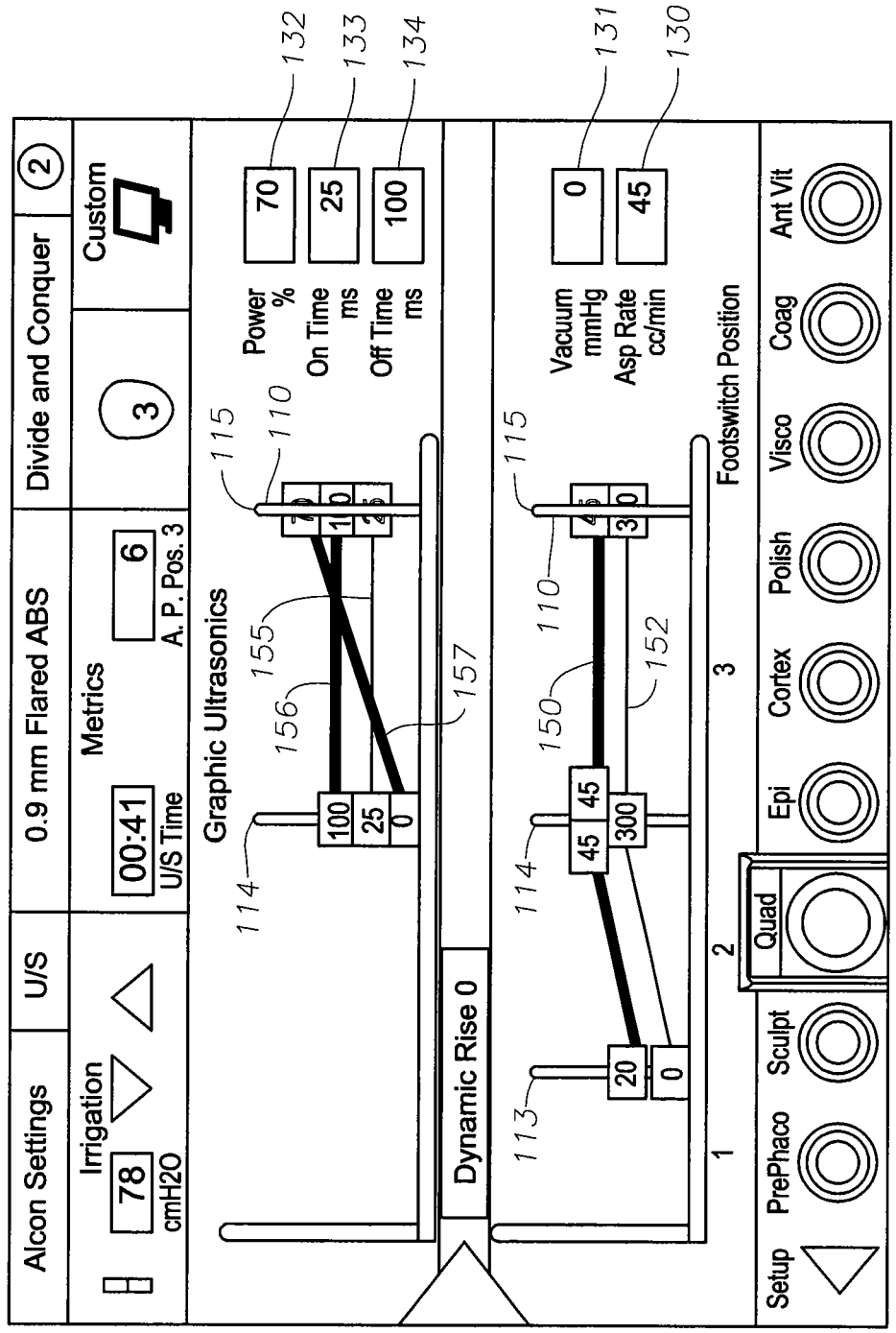
FIG. 18 illustrates representations of surgical device parameters relative to a representation of a foot pedal positioned at the end of a third stage or range of positions and the corresponding current values of the parameters invoked the foot pedal position.

FIG. 17 illustrates the foot pedal being depressed further so that the representation 110, approaches the boundary line 115. The power 157 linearly increases to 58%, and the on time, off time, vacuum and aspiration rate remain the same. When the foot pedal is pushed all the way down and the foot pedal representation 110 is to the far right, as shown in FIG. 18, the power 157 is maximum at 70%, and the on time, off time, vacuum and aspiration rates remain the same.

Persons skilled in the art will appreciate that the illustrated sequence of steps or stages do not necessarily occur in the exact sequential order described. Rather, a surgeon may randomly and periodically alternate between pressing and releasing the foot pedal, thus switching between various stages and involving different operating parameters and different parameter values. Accordingly, the sequence shown in FIGS. 12-18 is only to illustrate how foot pedal displacement is represented and invokes operating parameters, as displayed on the display screen relative to foot pedal displacement.

Figure 19:
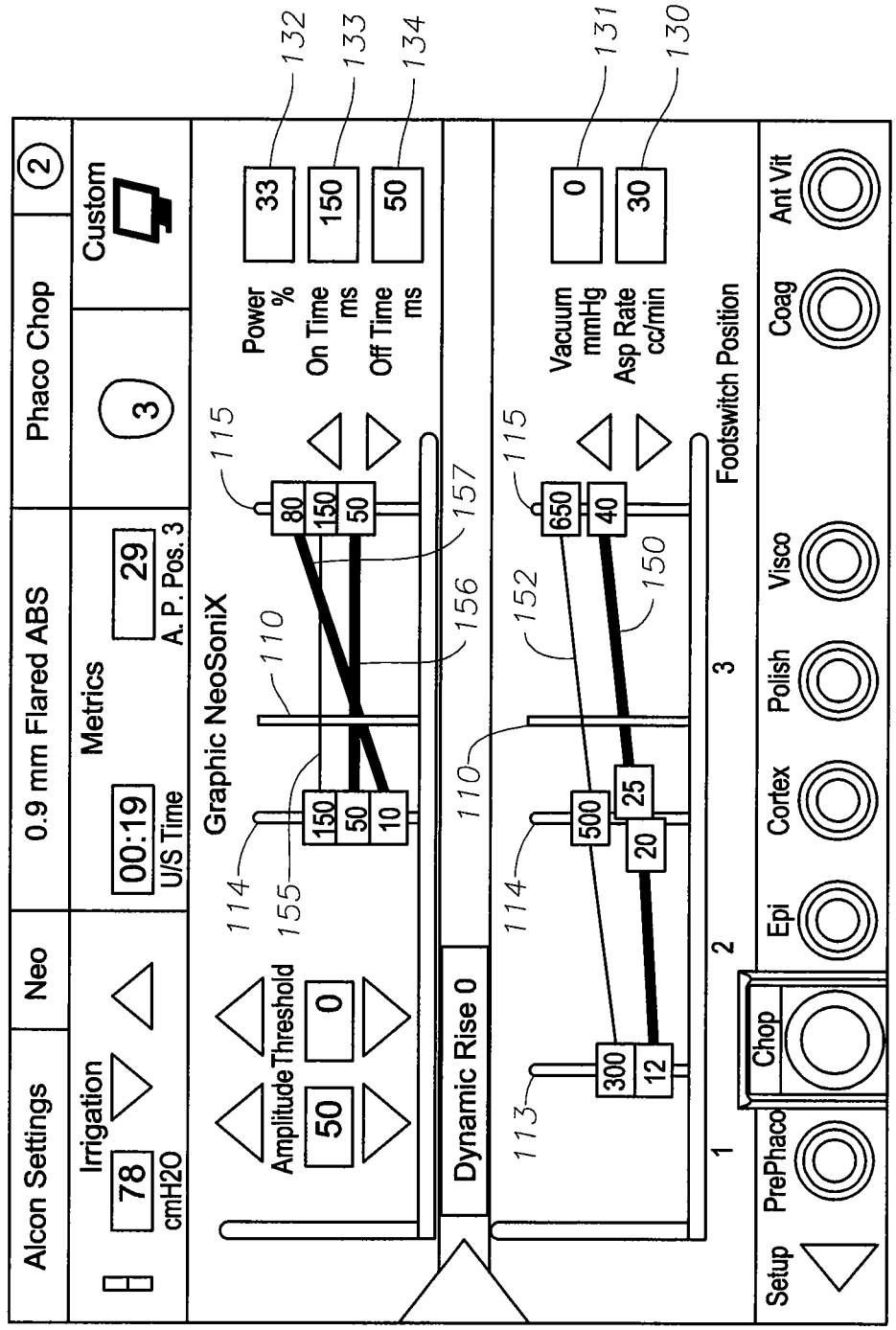
FIG. 19 illustrates another surgical interface embodiment that includes representations of parameters that are selected to provide pulsed ultrasound power that varies linearly.

FIG. 19 illustrates another embodiment in which the initial ultrasound power value 153 when ultrasound power 157 is initiated is greater than zero, and the aspiration rate 150 and the end of the first stage and the aspiration rate 150 at the beginning of the second stage are different. In this embodiment, the aspiration flow rate 150 is fixed at 45 cc/min throughout stages 2 and 3. These control parameters allow vacuum to continuously increase throughout stages 2 and 3, which can be difficult to implement conventional graphical user interfaces that would otherwise require additional numerical values on the display screen, thereby complicating the appearance of the screen and the ability to understand the parameter settings, particularly during a surgical procedure.

Figure 20:
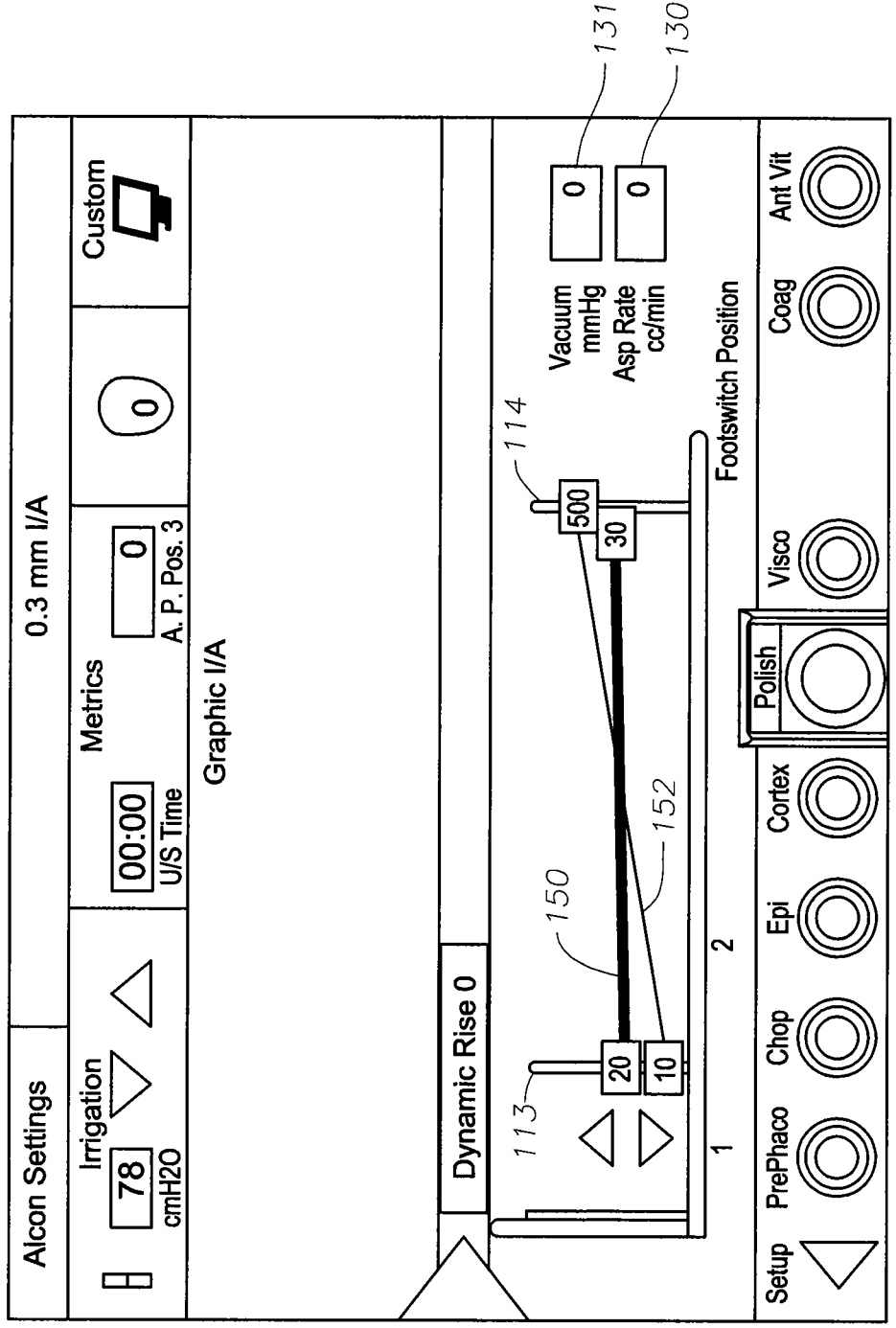
FIG. 20 illustrates an interface having representations of aspiration rate and vacuum that both increase linearly.

FIG. 20 illustrates an alternative embodiment with controls for fluidics only. Since no ultrasound is used, there is no representation of Stage 3 associated with the ultrasound.

Figure 21:
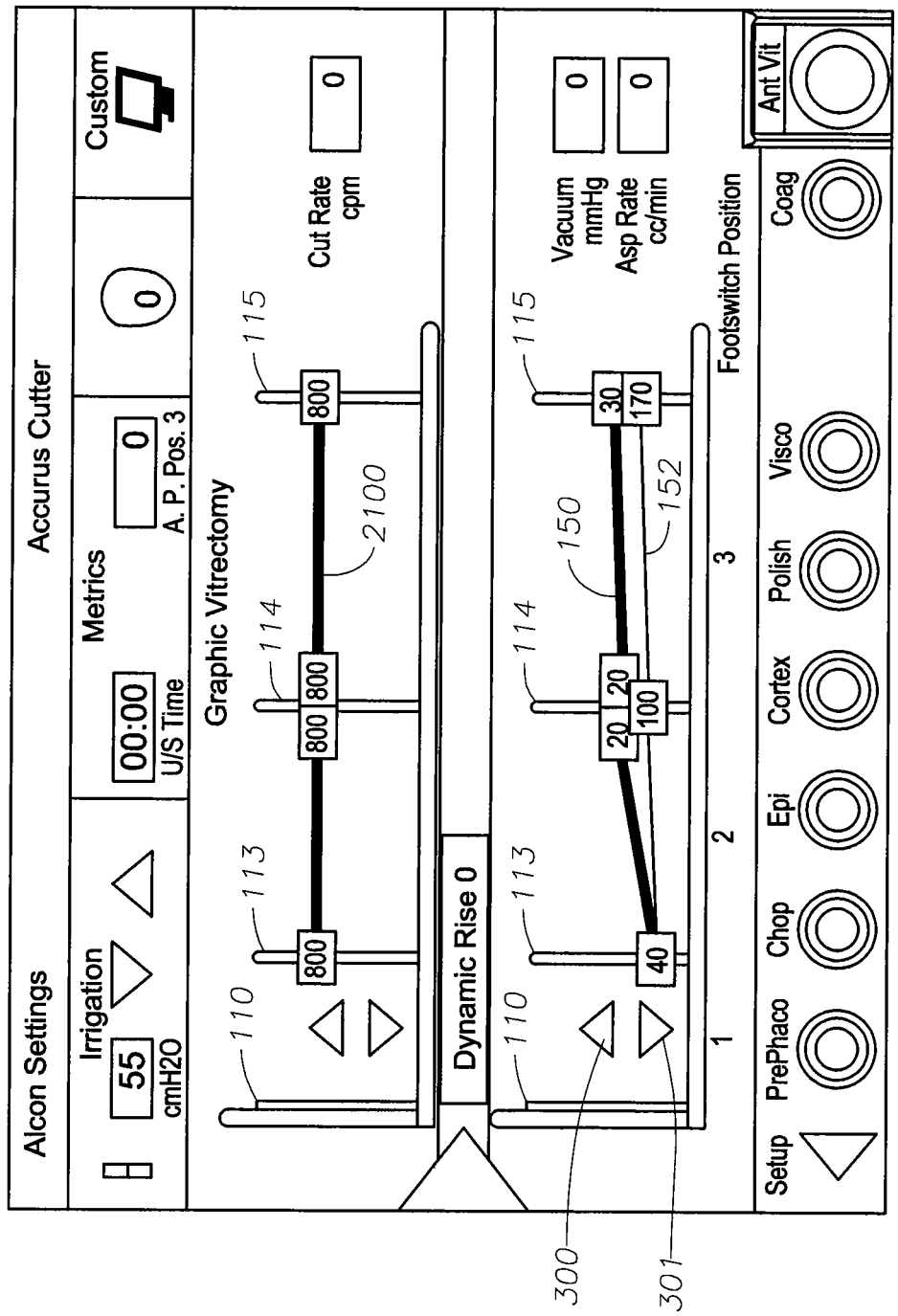
FIG. 21 illustrates an interface having representations of cutting rate, aspiration rate and vacuum for use with a guillotine cutter.
Figure 22:
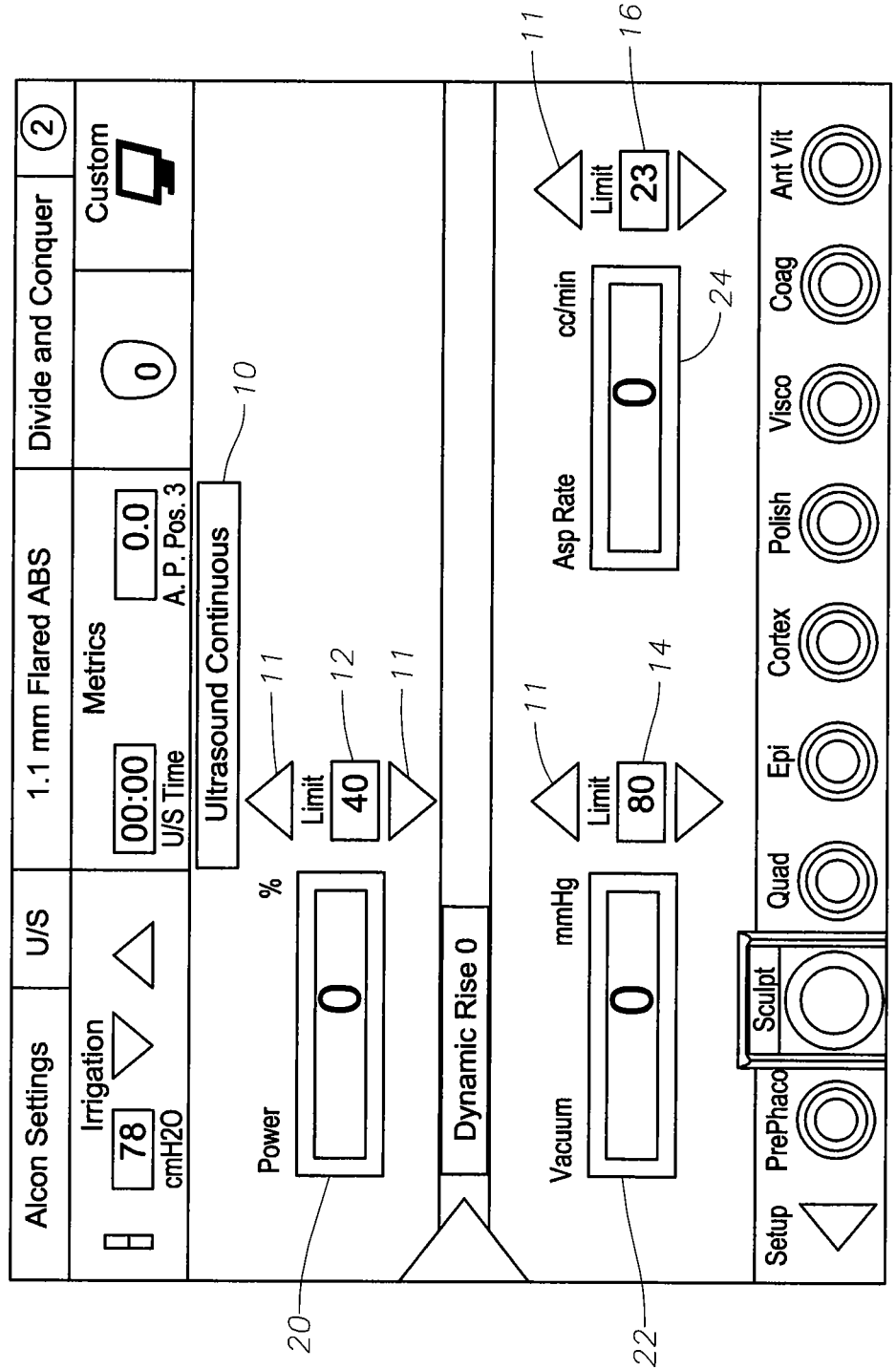
FIG. 22 illustrates a known graphical user interface that includes fixed fields and adjustment arrows to change parameter values for continuous ultrasound power.
Figure 23:
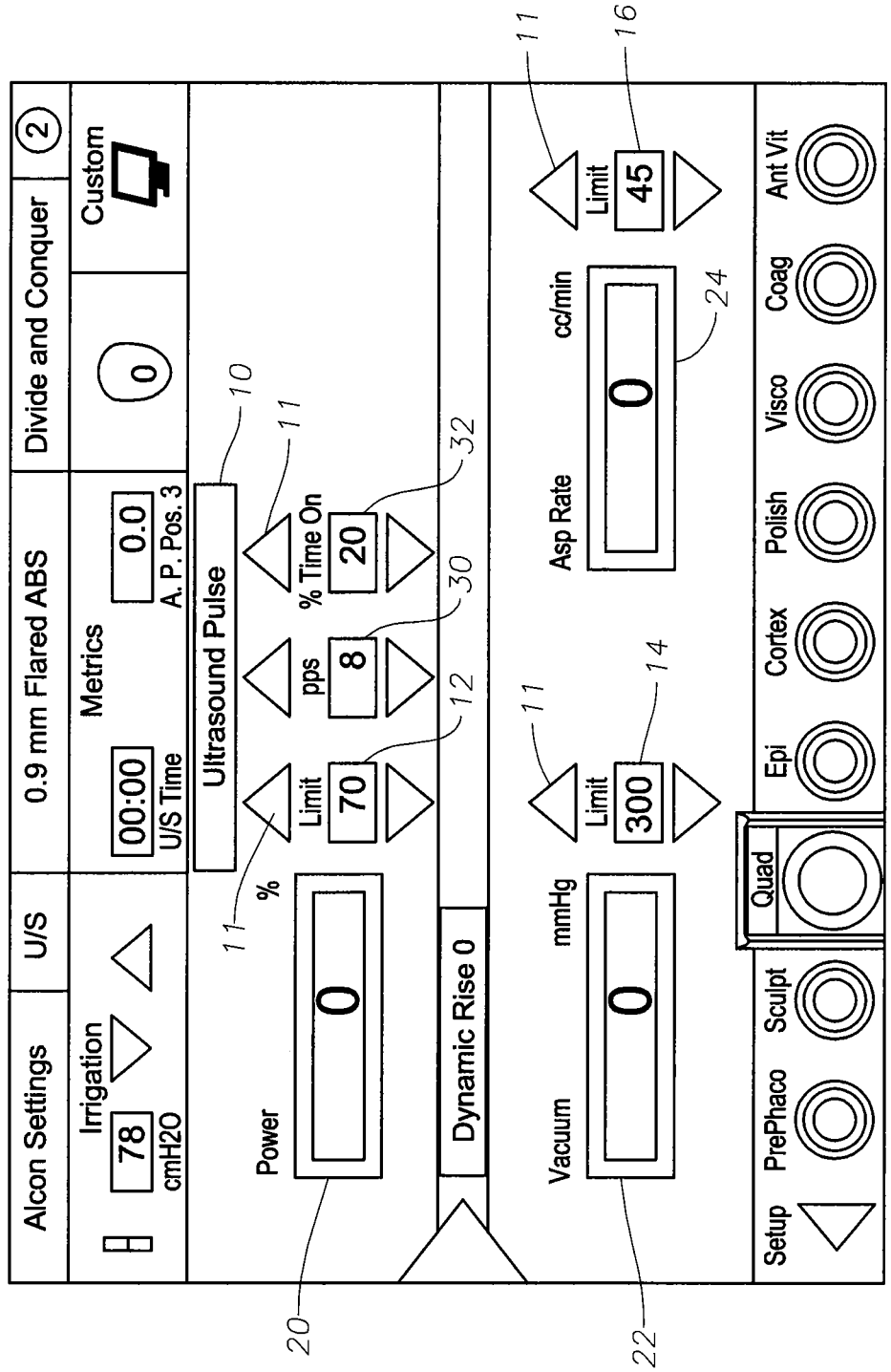
FIG. 23 illustrates another known graphical user interface with adjustment arrows and the interface parameters being set for pulsed ultrasound power.

FIG. 21 illustrates an embodiment which shows control of an anterior vitrectomy guillotine cutter in the upper half of the screen and control of flow 150 and vacuum 152 in the lower part of the screen. These settings allow the cutter to turn on at maximum speed of 800 cuts per minute 2100 at the beginning of the Stage 2 when flow rate 150 is set to approximately 10 cc/min and the vacuum limit 152 is set to 40 cc/min. As the foot pedal is depressed further, the flow rate 150 and vacuum limit 152 increase while the cutting speed 2100 remains substantially constant.

Persons of ordinary skill in the art will appreciate that the representations of operating parameters can be selected and adjusted to control surgical devices in various manners, with different combinations of fixed vacuum, varying vacuum, fixed aspiration, varying aspiration, fixed off time, variable off time, fixed on time, variable on time, and power increasing or decreasing between various levels. Accordingly, interfaces including representations of control parameters shown in FIGS. 1-21 are not intended to be limiting, as many other control settings can be used by making the required adjustments to the parameter representations.

Further, persons skilled in the art will appreciate that embodiments can be applied to other surgical system and other control mechanisms, besides a phacoemulsification system that uses a foot pedal. Additionally, embodiments can be applied to display and control other operating parameters that may be associated with a particular surgery. Moreover, although this specification has described and illustrated parameters that are fixed or constant and linear, operating parameters may be programmed to behave according to other functions. For example, rather than linear power during stage 3, power may be controlled according to a logarithmic function, an exponential function, a polynomial function, and other functions. As a further example, aspiration can be controlled between different boundary lines according to these and other alternative functions. The representation of the control parameter may also assume a shape representing the particular function. Alternatively, the representation can appear as a straight line, but be programmed according to another function. Accordingly, embodiments provide significant flexibility in displaying and controlling various operating parameters on a display screen as the needs of a particular surgical device or procedure require.

Having described interface system and method embodiments, persons skilled in the art will recognize that the above system and method of operating can be modified in various ways to perform the same interface and control functions. Accordingly, persons of ordinary skill in the art will appreciate that embodiments are not limited to the particular exemplary embodiments described, but rather, embodiments can be applied to other surgical equipment and parameters. Although references have been made in the foregoing description to various embodiments, persons of ordinary skill in the art of interfaces for surgical systems and related systems will recognize that insubstantial modifications, alterations, and substitutions can be made to the described embodiments without departing from the invention as claimed in the accompanying claims.

What is claimed:

1. An interface for displaying and controlling parameters related to the operation of a surgical device, the parameters being displayed on a display screen, the interface comprising:
a graphical user interface, the graphical user interface being displayed on the display screen, the graphical user interface including representations of the parameters, at least one of the representations being a linear representation having a first end and a second end, the first end representing a minimum value of the parameter, the second end representing a maximum value of the parameter, the at least one parameter being adjustable by moving at least one of the first end and the second end from a first location on the display screen to a second location on the display screen, thereby controlling the operation of the surgical device.

2. The interface of claim 1, the graphical user interface including a numerical field, the numerical field being located at the first end of the linear representation and indicating the minimum value of the parameter.

3. The interface of claim 1, the graphical user interface including a numerical field, the numerical field being located at the second end of the linear representation and indicating the maximum value of the parameter.

4. The interface of claim 1, wherein the representation is that of a parameter that operates according to a linear, a logarithmic, an exponential or a polynomial function between the first and second ends of the linear representation.

5. The interface of claim 1, the minimum value being user-adjustable between zero and an intermediate value that is greater than zero.

6. The interface of claim 1, the graphical user interface including one or more numerical fields that are separate from the representations, the numerical fields indicating a current power level, a current duration of power, a current vacuum pressure, or a current aspiration rate.

7. The interface of claim 1, the graphical user interface including a representation of stages of a surgical procedure involving the surgical device.

8. The interface of claim 7, the representation of the parameters being displayed relative to the representation of the stages of the surgical procedure.

9. The interface of claim 7, the representation of stages being vertical dividers, a stage of the surgical procedure being defined between two vertical dividers.

10. The interface of claim 9, the representation of the parameter being adjustable by moving the first end or the second end of the representation of the parameter along a vertical divider.

11. The interface of claim 9, the representation of the parameter extending between two vertical dividers.

12. The interface of claim 9, a vertical divider defining a stage at which irrigation, aspiration or ultrasound power begins.

13. The interface of claim 9, wherein the representations of the parameters comprises a plurality of representations of parameters extending between the a first vertical divider and a second vertical divider,
wherein each of the plurality of representations of parameters has a first end at a location along the first vertical divider and a second end at a location along the second vertical divider,
wherein the first ends of each of the plurality of representations of parameters are moveable along the first vertical divider independently of each other to adjust the minimum value of the respective parameters, and
wherein the second ends of each of the plurality of representations of parameters are moveable along the second divider independently of each other to adjust the maximum value of the respective parameters.

14. The interface of claim 1, wherein the first end is moveable along a first vertical divider to adjust the minimum value of the parameter, and wherein the second end is moveable along a second vertical divider to adjust the maximum value of the parameter.

15. The interface of claim 1, the graphical user interface including a representation of a control member for use in operating the surgical device.

16. The interface of claim 15, the control member being a foot pedal.

17. The interface of claim 15, the representation of the parameter being displayed relative to the representation of the control member.

18. The interface of claim 15, the graphical user interface including a representation of stages of a surgical procedure involving the surgical device, the representation of the control member being moveable between the stages of the surgical procedure by displacement of the control member.

19. The interface of claim 18, the representation of the control member being a vertical line, the vertical line being moveable horizontally to indicate the stage of the surgical procedure.

20. The interface of claim 1, the graphical user interface being split into first and second sections, the first section including a representation of power.

21. The interface of claim 20, the second section including a representation of vacuum or aspiration.

22. The interface of claim 20, the second section including a representation of stages of the surgical procedure.

23. The interface of claim 20, the first interface section being above the second interface section.

24. The interface of claim 1, the surgical device being a phacoemulsification device.

25. The interface of claim 1, the parameter representations being adjustable to provide continuous, pulsed power or burst power.

26. The system of claim 1, the parameters representations being adjustable to provide power that varies linearly.

27. A system for displaying and controlling operation parameters of a surgical device used in a phacoemulsification procedure, the system comprising:
a display screen; and
a graphical user interface, the graphical user interface being displayed on the display screen, the graphical user interface including representations of parameters related to the operation of the surgical device and a representation of stages of the phacoemulsification procedure, the representations of the parameters being shown relative to the representations of the stages of the phacoemulsification procedure, one or more of the parameter representations being a linear representation, the linear representation having a first end and a second end, the first end representing a minimum value of the parameter, the second end representing a maximum value of the parameter, the parameters being adjustable by touching and dragging at least one of the first and second ends from a first location on the display screen to a second location on the display screen, thereby controlling the operation of the surgical device.

28. The system of claim 27, the graphical user interface including a numerical field, the numerical field being located at the first end of the linear representation and indicating the minimum value of the parameter.

29. The system of claim 27, the graphical user interface including a numerical field, the numerical field being located at the second end of the linear representation and indicating the maximum value of the parameter.

30. The system of claim 27, the representation being a representation of a parameter that operates according to a linear, a logarithmic, an exponential or a polynomial function between the first and second ends of the linear representation.

31. The system of claim 27, the minimum value being user-adjustable between zero and an intermediate value that is greater than zero.

32. The system of claim 27, the graphical user interface including a numerical field that is separate from the parameter representations and that indicates a current power level, a current duration of power, a current vacuum pressure, or a current aspiration rate.

33. The system of claim 27, the representation of stages being vertical dividers, a stage of the phacoemulsification procedure being defined between two vertical dividers.

34. The system of claim 33, the one or more of the parameter representations being adjustable by moving an end of the parameter representation along a vertical divider.

35. The system of claim 33, the representation of the parameter extending between two vertical dividers.

36. The system of claim 33, a vertical divider defining a stage at which irrigation, aspiration or ultrasound power begins.

37. The system of claim 27, the graphical user interface including a representation of a control member for use in operating the surgical device.

38. The system of claim 37, the control member being a foot pedal.

39. The system of claim 37, the representation of the parameter being displayed relative to the representation of the control member.

40. The system of claim 37, the representation of the control member being moveable between the representation of stages of the phacoemulsification procedure by displacement of the control member.

41. The system of claim 37, the representation of the control member being a vertical line, the vertical line being moveable horizontally to indicate the stage of the surgical procedure.

42. The system of claim 27, the graphical user interface being split into first and second sections, the first section including a representation of power.

43. The system of claim 42, the second section including a representation of vacuum and aspiration rate.

44. The system of claim 42, the first interface section being above the second interface section.

45. The system of claim 27, the parameter being adjustable to provide continuous, pulsed, or burst power.

46. The system of claim 27, the parameter representations being adjustable to provide power that varies linearly.

47. An interface for displaying and controlling a parameter related to the operation of a surgical device, the parameter being displayed on a display screen, the interface comprising:

a graphical user interface, the graphical user interface being displayed on the display screen, the graphical user interface including a representation of the parameter related to the operation of the surgical device and a representation of stages of a surgical procedure, the representation of the parameter being shown relative to the representation of the stages of the phacoemulsification procedure, the representation having a first end representing a minimum value of the parameter, the second end representing a maximum value of the parameter, the parameters being adjustable by moving at least one of the first end and second end from a first location on the display screen to a second location on the display screen, thereby controlling the operation of the surgical device.

* * * * *